(12) United States Patent
Monti

(10) Patent No.: US 11,925,412 B2
(45) Date of Patent: Mar. 12, 2024

(54) GAZE TRACKING APPARATUS AND SYSTEMS

(71) Applicant: Sony Interactive Entertainment Inc., Tokyo (JP)

(72) Inventor: Maria Chiara Monti, London (GB)

(73) Assignee: Sony Interactive Entertainment Inc., Tokyo (JP)

( * ) Notice: Subject to any disclaimer, the term of this patent is extended or adjusted under 35 U.S.C. 154(b) by 272 days.

(21) Appl. No.: 17/333,350

(22) Filed: May 28, 2021

(65) Prior Publication Data

US 2021/0378504 A1 Dec. 9, 2021

(30) Foreign Application Priority Data

Jun. 4, 2020 (GB) .................................... 2008417

(51) Int. Cl.
| | | |
|---|---|---|
| *A61B 3/10* | (2006.01) | |
| *A61B 3/00* | (2006.01) | |
| *A61B 3/02* | (2006.01) | |
| *A61B 3/024* | (2006.01) | |
| *A61B 3/113* | (2006.01) | |
| *G02B 27/00* | (2006.01) | |
| *G02B 27/01* | (2006.01) | |

(52) U.S. Cl.
CPC .......... *A61B 3/0091* (2013.01); *A61B 3/0033* (2013.01); *A61B 3/0041* (2013.01); *A61B 3/113* (2013.01); *G02B 27/0093* (2013.01); *G02B 27/0101* (2013.01); *G02B 27/0172* (2013.01); *G02B 2027/0123* (2013.01)

(58) Field of Classification Search
CPC ......... A61B 3/1025; A61B 3/02; A61B 3/102; A61B 3/113; A61B 3/1015; A61B 3/103; A61B 3/1225; A61B 3/024; A61B 3/032; A61B 3/005
USPC ........ 351/206, 200, 205, 209–211, 221–223, 351/239, 243, 245, 246
See application file for complete search history.

(56) References Cited

U.S. PATENT DOCUMENTS

| | | | |
|---|---|---|---|
| 6,386,706 B1 * | 5/2002 | McClure | A61B 3/024 351/237 |
| 9,955,862 B2 | 5/2018 | Freeman | |
| 10,331,207 B1 | 6/2019 | Simmons | |
| 10,674,127 B1 | 6/2020 | Abou Shousha | |
| 2015/0238362 A1 | 8/2015 | Chayet | |

(Continued)

OTHER PUBLICATIONS

Extended European Search Report for corresponding to EP Application No. 21176071.5, 9 pages, dated Nov. 2, 2021.

(Continued)

*Primary Examiner* — Dawayne Pinkney
(74) *Attorney, Agent, or Firm* — Matthew B. Dernier, Esq.

(57) ABSTRACT

A head-mountable display (HMD) system includes at least one detector to detect a gaze direction of an eye of a user wearing the HMD, receiving circuitry to receive a user input from the user indicating a type of eye condition for the eye of the user associated with at least partial vision loss for a region of vision, a display unit to display one or more images to the user, and a processor to generate the one or more images for display to the user by the display unit in dependence upon the type of eye condition and an output of the at least one detector indicative of the detected gaze direction of the eye.

20 Claims, 12 Drawing Sheets

(56) References Cited

U.S. PATENT DOCUMENTS

| | | |
|---|---|---|
| 2016/0270656 A1 | 9/2016 | Samec |
| 2017/0200296 A1 | 7/2017 | Jones |
| 2017/0365189 A1* | 12/2017 | Halpin ................. G09B 21/008 |
| 2019/0179409 A1 | 6/2019 | Jones |
| 2019/0339528 A1 | 11/2019 | Freeman |

OTHER PUBLICATIONS

Combined Search and Examination Report for corresponding to GB2008417.4, 7 pages, dated Dec. 2, 2020.

* cited by examiner

GAZE TRACKING APPARATUS AND SYSTEMS

BACKGROUND OF THE INVENTION

Field of the Invention

This invention relates to gaze tracking apparatus and systems.

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

Gaze tracking systems are used to identify a location of a subject's gaze within an environment; in many cases, this location may be a position on a display screen that is being viewed by the subject. In a number of existing arrangements, this is performed using one or more inwards-facing cameras directed towards the subject's eye (or eyes) in order to determine a direction in which the eyes are oriented at any given time. Having identified the orientation of the eye, a gaze direction can be determined and a focal region may be determined as the intersection of the gaze direction of each eye.

One application for which gaze tracking is considered of particular use is that of use in head-mountable display units (HMDs). The use in HMDs may be of particular benefit owing to the close proximity of inward-facing cameras to the user's eyes, allowing the tracking to be performed much more accurately and precisely than in arrangements in which it is not possibly to provide the cameras with such proximity.

By utilising gaze detection techniques, it may be possible to provide a more efficient and/or effective processing method for generating content or interacting with devices.

For example, gaze tracking may be used to provide user inputs or to assist with such inputs—a continued gaze at a location may act as a selection, or a gaze towards a particular object accompanied by another input (such as a button press) may be considered as a suitable input. This may be more effective as an input method in some embodiments, particularly in those in which a controller is not provided or when a user has limited mobility.

Foveal rendering is an example of a use for the results of a gaze tracking process in order to improve the efficiency of a content generation process. Foveal rendering is rendering that is performed so as to exploit the fact that human vision is only able to identify high detail in a narrow region (the fovea), with the ability to discern detail tailing off sharply outside of this region.

In such methods, a portion of the display is identified as being an area of focus in accordance with the user's gaze direction. This portion of the display is supplied with high-quality image content, while the remaining areas of the display are provided with lower-quality (and therefore less resource intensive to generate) image content. This can lead to a more efficient use of available processing resources without a noticeable degradation of image quality for the user.

It is therefore considered advantageous to be able to improve gaze tracking methods, and/or apply the results of such methods in an improved manner. It is in the context of such advantages that the present disclosure arises.

SUMMARY OF THE INVENTION

Various aspects and features of the present invention are defined in the appended claims and within the text of the accompanying description.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DESCRIPTION OF THE EMBODIMENTS

Figure 1:
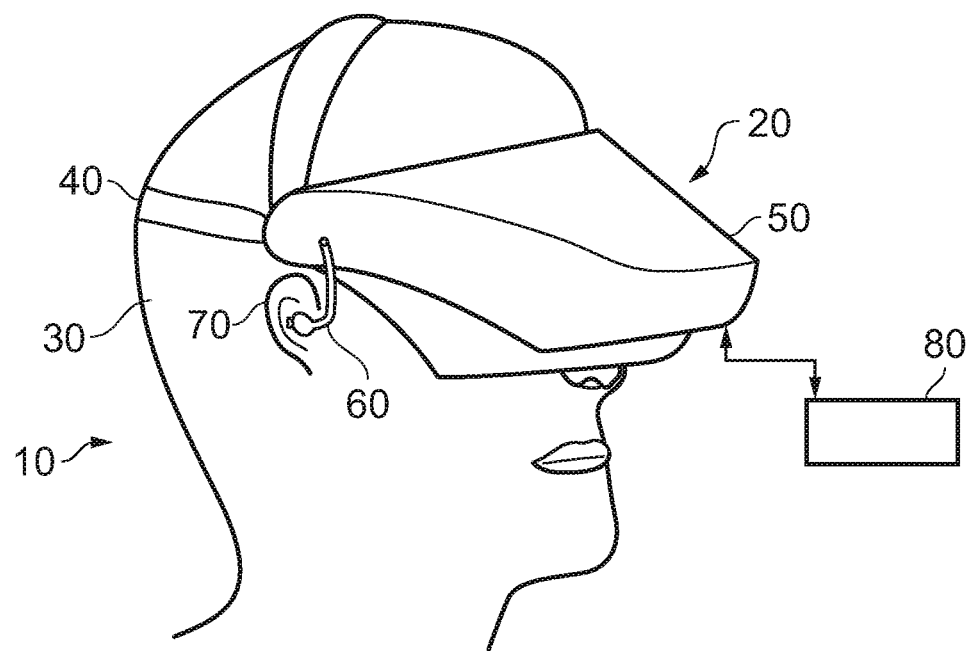
FIG. 1 schematically illustrates an HMD worn by a user.

Referring now to the drawings, wherein like reference numerals designate identical or corresponding parts throughout the several views, in FIG. 1 a user 10 is wearing an HMD 20 (as an example of a generic head-mountable apparatus—other examples including audio headphones or a head-mountable light source) on the user's head 30. The HMD comprises a frame 40, in this example formed of a rear strap and a top strap, and a display portion 50. As noted above, many gaze tracking arrangements may be considered particularly suitable for use in HMD systems; however, use with such an HMD system should not be considered essential.

Note that the HMD of FIG. 1 may comprise further features, to be described below in connection with other drawings, but which are not shown in FIG. 1 for clarity of this initial explanation.

The HMD of FIG. 1 completely (or at least substantially completely) obscures the user's view of the surrounding environment. All that the user can see is the pair of images displayed within the HMD, as supplied by an external processing device such as a games console in many embodiments. Of course, in some embodiments images may instead (or additionally) be generated by a processor or obtained from memory located at the HMD itself.

The HMD has associated headphone audio transducers or earpieces 60 which fit into the user's left and right ears 70. The earpieces 60 replay an audio signal provided from an external source, which may be the same as the video signal source which provides the video signal for display to the user's eyes.

The combination of the fact that the user can see only what is displayed by the HMD and, subject to the limitations of the noise blocking or active cancellation properties of the earpieces and associated electronics, can hear only what is provided via the earpieces, mean that this HMD may be considered as a so-called "full immersion" HMD. Note however that in some embodiments the HMD is not a full immersion HMD, and may provide at least some facility for the user to see and/or hear the user's surroundings. This could be by providing some degree of transparency or partial transparency in the display arrangements, and/or by projecting a view of the outside (captured using a camera, for example a camera mounted on the HMD) via the HMD's displays, and/or by allowing the transmission of ambient sound past the earpieces and/or by providing a microphone to generate an input sound signal (for transmission to the earpieces) dependent upon the ambient sound.

A front-facing camera 122 may capture images to the front of the HMD, in use. Such images may be used for head tracking purposes, in some embodiments, while it may also be suitable for capturing images for an augmented reality (AR) style experience. A Bluetooth® antenna 124 may provide communication facilities or may simply be arranged as a directional antenna to allow a detection of the direction of a nearby Bluetooth® transmitter.

In operation, a video signal is provided for display by the HMD. This could be provided by an external video signal source 80 such as a video games machine or data processing apparatus (such as a personal computer), in which case the signals could be transmitted to the HMD by a wired or a wireless connection. Examples of suitable wireless connections include Bluetooth® connections. Audio signals for the earpieces 60 can be carried by the same connection. Similarly, any control signals passed from the HMD to the video (audio) signal source may be carried by the same connection. Furthermore, a power supply 83 (including one or more batteries and/or being connectable to a mains power outlet) may be linked by a cable to the HMD. Note that the power supply 83 and the video signal source 80 may be separate units or may be embodied as the same physical unit. There may be separate cables for power and video (and indeed for audio) signal supply, or these may be combined for carriage on a single cable (for example, using separate conductors, as in a USB cable, or in a similar way to a "power over Ethernet" arrangement in which data is carried as a balanced signal and power as direct current, over the same collection of physical wires). The video and/or audio signal may be carried by, for example, an optical fibre cable. In other embodiments, at least part of the functionality associated with generating image and/or audio signals for presentation to the user may be carried out by circuitry and/or processing forming part of the HMD itself. A power supply may be provided as part of the HMD itself.

Some embodiments of the invention are applicable to an HMD having at least one electrical and/or optical cable linking the HMD to another device, such as a power supply and/or a video (and/or audio) signal source. So, embodiments of the invention can include, for example:

(a) an HMD having its own power supply (as part of the HMD arrangement) but a cabled connection to a video and/or audio signal source;

(b) an HMD having a cabled connection to a power supply and to a video and/or audio signal source, embodied as a single physical cable or more than one physical cable;

(c) an HMD having its own video and/or audio signal source (as part of the HMD arrangement) and a cabled connection to a power supply; or (d) an HMD having a wireless connection to a video and/or audio signal source and a cabled connection to a power supply.

If one or more cables are used, the physical position at which the cable enters or joins the HMD is not particularly important from a technical point of view. Aesthetically, and to avoid the cable(s) brushing the user's face in operation, it would normally be the case that the cable(s) would enter or join the HMD at the side or back of the HMD (relative to the orientation of the user's head when worn in normal operation). Accordingly, the position of the cables relative to the HMD in FIG. 1 should be treated merely as a schematic representation.

Accordingly, the arrangement of FIG. 1 provides an example of a head-mountable display system comprising a frame to be mounted onto an observer's head, the frame defining one or two eye display positions which, in use, are positioned in front of a respective eye of the observer and a display element (display unit) mounted with respect to each of the eye display positions, the display element providing a virtual image of a video display of a video signal from a video signal source to that eye of the observer.

FIG. 1 shows just one example of an HMD. Other formats are possible: for example an HMD could use a frame more similar to that associated with conventional eyeglasses, namely a substantially horizontal leg extending back from the display portion to the top rear of the user's ear, possibly curling down behind the ear. In other (not full immersion) examples, the user's view of the external environment may not in fact be entirely obscured; the displayed images could be arranged so as to be superposed (from the user's point of view) over the external environment. An example of such an arrangement will be described below with reference to FIG. 4.

Figure 2:
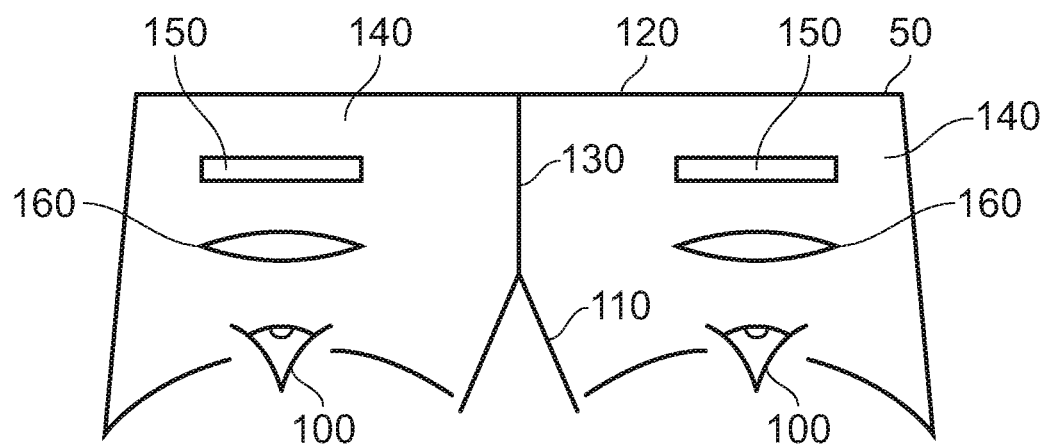
FIG. 2 is a schematic plan view of an HMD.

In the example of FIG. 1, a separate respective display is provided for each of the user's eyes. A schematic plan view of how this is achieved is provided as FIG. 2, which illustrates the positions 100 of the user's eyes and the relative position 110 of the user's nose. The display portion 50, in schematic form, comprises an exterior shield 120 to mask ambient light from the user's eyes and an internal shield 130 which prevents one eye from seeing the display intended for the other eye. The combination of the user's face, the exterior shield 120 and the interior shield 130 form two compartments 140, one for each eye. In each of the compartments there is provided a display element (display unit) 150 and one or more optical elements 160. The way in which the display element and the optical element(s) cooperate to provide a display to the user will be described with reference to FIG. 3.

Figure 3:
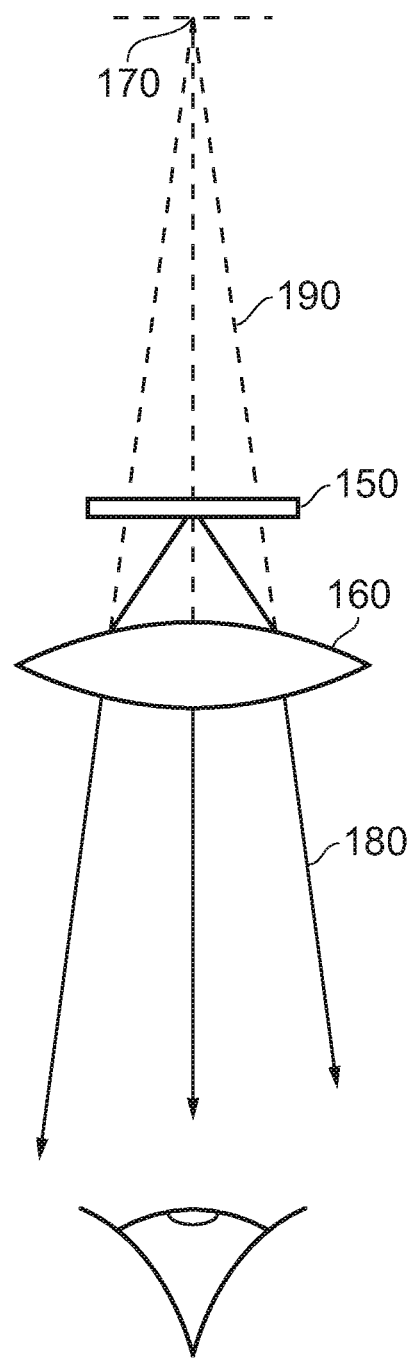
FIG. 3 schematically illustrates the formation of a virtual image by an HMD.

Referring to FIG. 3, the display element (display unit) 150 generates a displayed image which is (in this example) refracted by the optical elements 160 (shown schematically as a convex lens but which could include compound lenses or other elements) so as to generate a virtual image 170 which appears to the user to be larger than and significantly further away than the real image generated by the display element 150. As an example, the virtual image may have an apparent image size (image diagonal) of more than 1 m and may be disposed at a distance of more than 1 m from the user's eye (or from the frame of the HMD). In general terms, depending on the purpose of the HMD, it is desirable to have the virtual image disposed a significant distance from the user. For example, if the HMD is for viewing movies or the like, it is desirable that the user's eyes are relaxed during such viewing, which requires a distance (to the virtual image) of at least several metres. In FIG. 3, solid lines (such as the line 180) are used to denote real optical rays, whereas broken lines (such as the line 190) are used to denote virtual rays.

Figure 4:
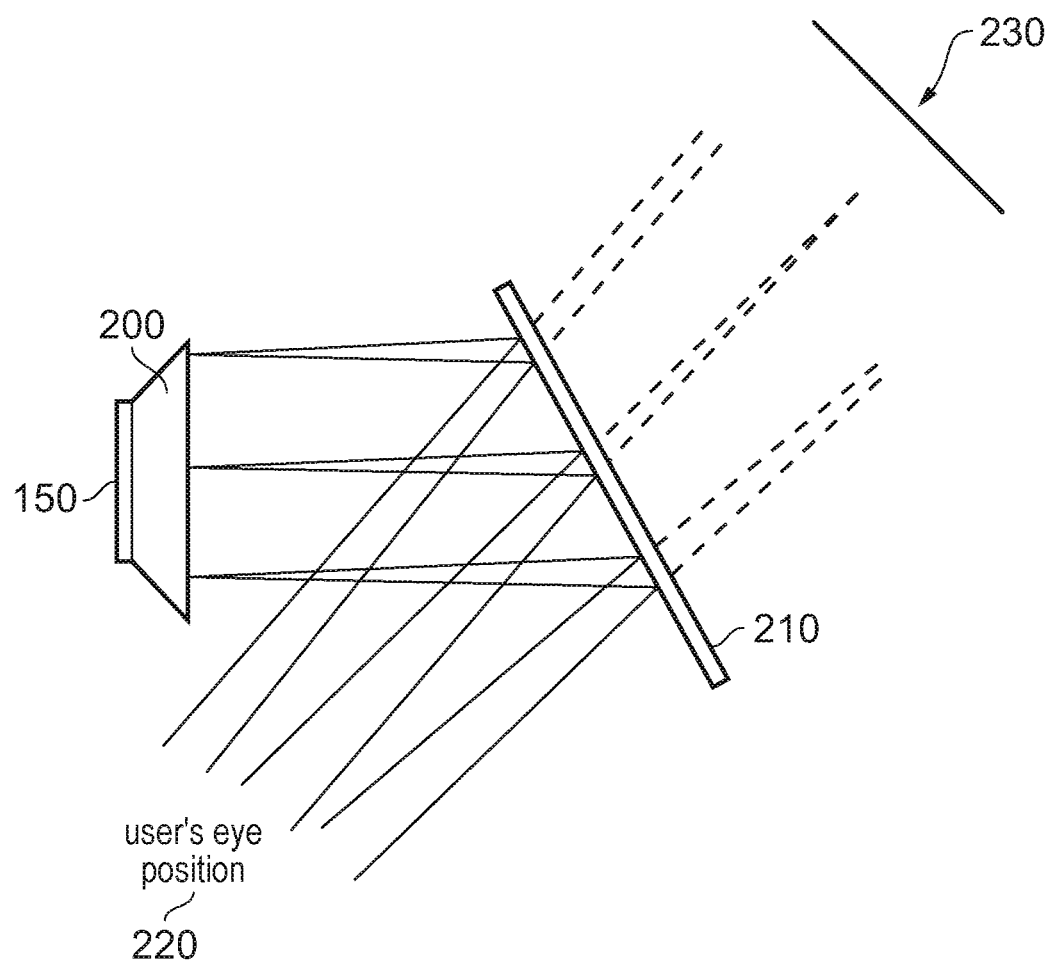
FIG. 4 schematically illustrates another type of display for use in an HMD.

An alternative arrangement is shown in FIG. 4. This arrangement may be used where it is desired that the user's view of the external environment is not entirely obscured. However, it is also applicable to HMDs in which the user's external view is wholly obscured. In the arrangement of FIG. 4, the display element (display unit) 150 and optical elements 200 cooperate to provide an image which is projected onto a mirror 210, which deflects the image towards the user's eye position 220. The user perceives a virtual image to be located at a position 230 which is in front of the user and at a suitable distance from the user.

In the case of an HMD in which the user's view of the external surroundings is entirely obscured, the mirror 210 can be a substantially 100% reflective mirror. The arrangement of FIG. 4 then has the advantage that the display element and optical elements can be located closer to the centre of gravity of the user's head and to the side of the user's eyes, which can produce a less bulky HMD for the user to wear. Alternatively, if the HMD is designed not to completely obscure the user's view of the external environment, the mirror 210 can be made partially reflective so that the user sees the external environment, through the mirror 210, with the virtual image superposed over the real external environment.

Figure 5:
FIG. 5 schematically illustrates a pair of stereoscopic images.

In the case where separate respective displays are provided for each of the user's eyes, it is possible to display stereoscopic images. An example of a pair of stereoscopic images for display to the left and right eyes is shown in FIG. 5. The images exhibit a lateral displacement relative to one another, with the displacement of image features depending upon the (real or simulated) lateral separation of the cameras by which the images were captured, the angular convergence of the cameras and the (real or simulated) distance of each image feature from the camera position.

Note that the lateral displacements in FIG. 5 could in fact be the other way round, which is to say that the left eye image as drawn could in fact be the right eye image, and the right eye image as drawn could in fact be the left eye image. This is because some stereoscopic displays tend to shift objects to the right in the right eye image and to the left in the left eye image, so as to simulate the idea that the user is looking through a stereoscopic window onto the scene beyond. However, some HMDs use the arrangement shown in FIG. 5 because this gives the impression to the user that the user is viewing the scene through a pair of binoculars. The choice between these two arrangements is at the discretion of the system designer.

In some situations, an HMD may be used simply to view movies and the like. In this case, there is no change required to the apparent viewpoint of the displayed images as the user turns the user's head, for example from side to side. In other uses, however, such as those associated with virtual reality (VR) or augmented reality (AR) systems, the user's viewpoint needs to track movements with respect to a real or virtual space in which the user is located.

As mentioned above, in some uses of the HMD, such as those associated with virtual reality (VR) or augmented reality (AR) systems, the user's viewpoint needs to track movements with respect to a real or virtual space in which the user is located.

This tracking is carried out by detecting motion of the HMD and varying the apparent viewpoint of the displayed images so that the apparent viewpoint tracks the motion. The detection may be performed using any suitable arrangement (or a combination of such arrangements). Examples include the use of hardware motion detectors (such as accelerometers or gyroscopes), external cameras operable to image the HMD, and outwards-facing cameras mounted onto the HMD.

Turning to gaze tracking in such an arrangement, FIG. 6 schematically illustrates two possible arrangements for performing eye tracking on an HMD. The cameras provided within such arrangements may be selected freely so as to be able to perform an effective eye-tracking method. In some existing arrangements, visible light cameras are used to capture images of a user's eyes. Alternatively, infra-red (IR) cameras are used so as to reduce interference either in the captured signals or with the user's vision should a corresponding light source be provided, or to improve performance in low-light conditions.

Figure 6A:
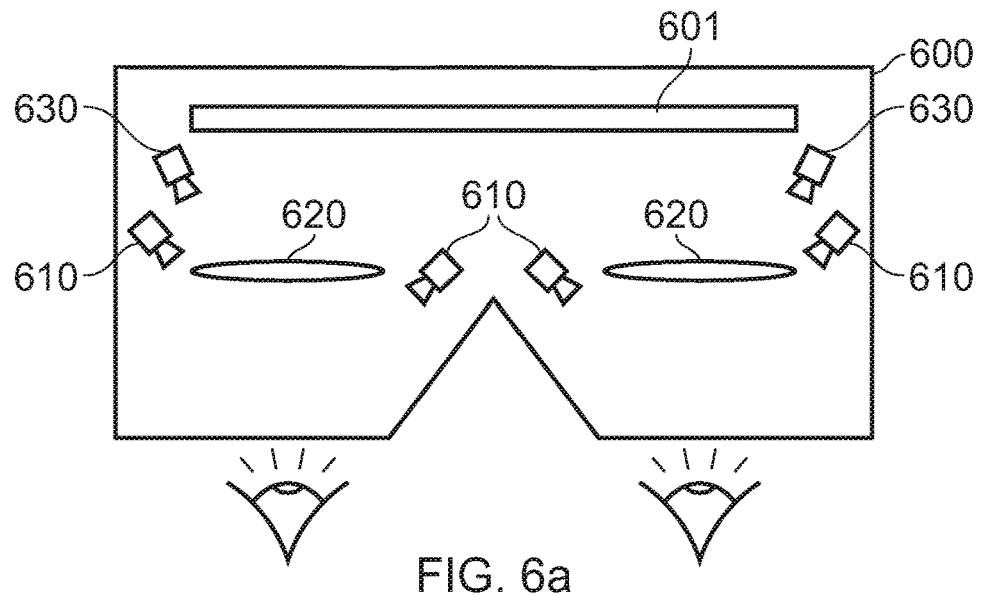
FIG. 6a schematically illustrates a plan view of an HMD.

FIG. 6a shows an example of a gaze tracking arrangement in which the cameras are arranged within an HMD so as to capture images of the user's eyes from a short distance. This may be referred to as near-eye tracking, or head-mounted tracking.

In this example, an HMD 600 with a display element (display unit) 601 is provided with cameras 610 that are each arranged so as to directly capture one or more images of a respective one of the user's eyes using an optical path that does not include the lens 620. This may be advantageous in that distortion in the captured image due to the optical effect of the lens is able to be avoided. Four cameras 610 are shown here as examples of possible positions that eye-tracking cameras may provided, although it should be considered that any number of cameras may be provided in any suitable location so as to be able to image the corresponding eye effectively. For example, only one camera may be provided per eye or more than two cameras may be provided for each eye.

However it is considered that in a number of embodiments it is advantageous that the cameras are instead arranged so as to include the lens 620 in the optical path used to capture images of the eye. Examples of such positions are shown by the cameras 630. While this may result in processing being required to enable suitably accurate tracking to be performed, due to the deformation in the captured image due to the lens, this may be performed relatively simply due to the fixed relative positions of the corresponding cameras and lenses. An advantage of including the lens within the optical path may be that of simplifying the physical constraints upon the design of an HMD, for example.

Figure 6B:
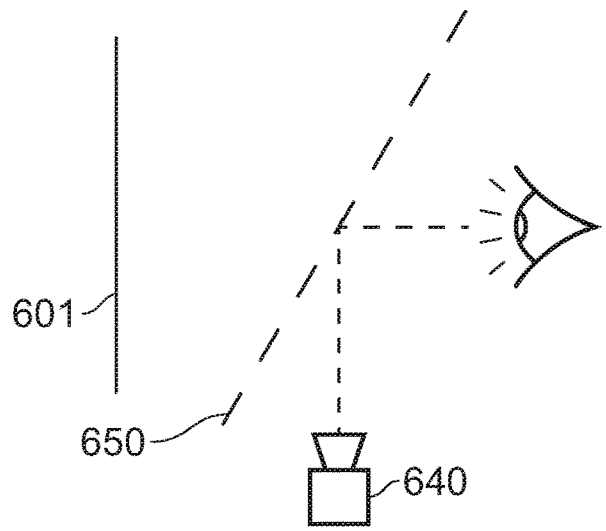
FIG. 6b schematically illustrates a near-eye tracking arrangement.

FIG. 6b shows an example of a gaze tracking arrangement in which the cameras are instead arranged so as to indirectly capture images of the user's eyes. Such an arrangement may be particularly suited to use with IR or otherwise non-visible light sources, as will be apparent from the below description.

FIG. 6b includes a mirror 650 arranged between a display 601 and the viewer's eye (of course, this can be extended to or duplicated at the user's other eye as appropriate). For the sake of clarity, any additional optics (such as lenses) are omitted in this Figure—it should be appreciated that they may be present at any suitable position within the depicted arrangement. The mirror 650 in such an arrangement is selected so as to be partially transmissive; that is, the mirror 650 should be selected so as to enable the camera 640 to obtain an image of the user's eye while the user views the display 601. One method of achieving this is to provide a mirror 650 that is reflective to IR wavelengths but transmissive to visible light—this enables IR light used for tracking to be reflected from the user's eye towards the camera 640 while the light emitted by the display 601 passes through the mirror uninterrupted.

Such an arrangement may be advantageous in that the cameras may be more easily arranged out of view of the user, for instance. Further to this, improvements to the accuracy of the eye tracking may be obtained due to the fact that the camera captures images from a position that is effectively (due to the reflection) along the axis between the user's eye and the display.

Figure 7:
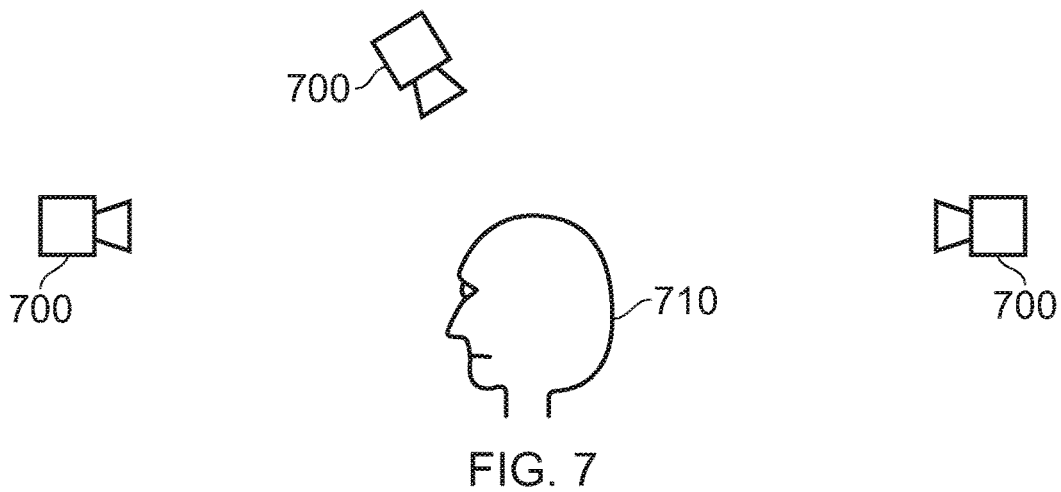
FIG. 7 schematically illustrates a remote tracking arrangement.

Of course, eye-tracking arrangements need not be implemented in a head-mounted or otherwise near-eye fashion as has been described above. For example, FIG. 7 schematically illustrates a system in which a camera is arranged to capture images of the user from a distance; this distance may vary during tracking, and may take any value in dependence upon the parameters of the tracking system. For example, this distance may be thirty centimetres, a metre, five metres, ten metres, or indeed any value so long as the tracking is not performed using an arrangement that is affixed to the user's head.

In FIG. 7, an array of cameras 700 is provided that together provide multiple views of the user 710. These cameras are configured to capture information identifying at least the direction in which a user's 710 eyes are focused, using any suitable method. For example, IR cameras may be utilised to identify reflections from the user's 710 eyes. An array of cameras 700 may be provided so as to provide multiple views of the user's 710 eyes at any given time, or may be provided so as to simply ensure that at any given time at least one camera 700 is able to view the user's 710 eyes. It is apparent that in some use cases it may not be necessary to provide such a high level of coverage and instead only one or two cameras 700 may be used to cover a smaller range of possible viewing directions of the user 710.

Of course, the technical difficulties associated with such a long-distance tracking method may be increased; higher resolution cameras may be required, as may stronger light sources for generating IR light, and further information (such as head orientation of the user) may need to be input to determine a focus of the user's gaze. The specifics of the arrangement may be determined in dependence upon a required level of robustness, accuracy, size, and/or cost, for example, or any other design consideration.

Despite technical challenges including those discussed above, such tracking methods may be considered beneficial in that they allow a greater range of interactions for a user—rather than being limited to HMD viewing, gaze tracking may be performed for a viewer of a television, for instance.

Rather than varying only in the location in which cameras are provided, eye-tracking arrangements may also differ in where the processing of the captured image data to determine tracking data is performed.

Figure 8:
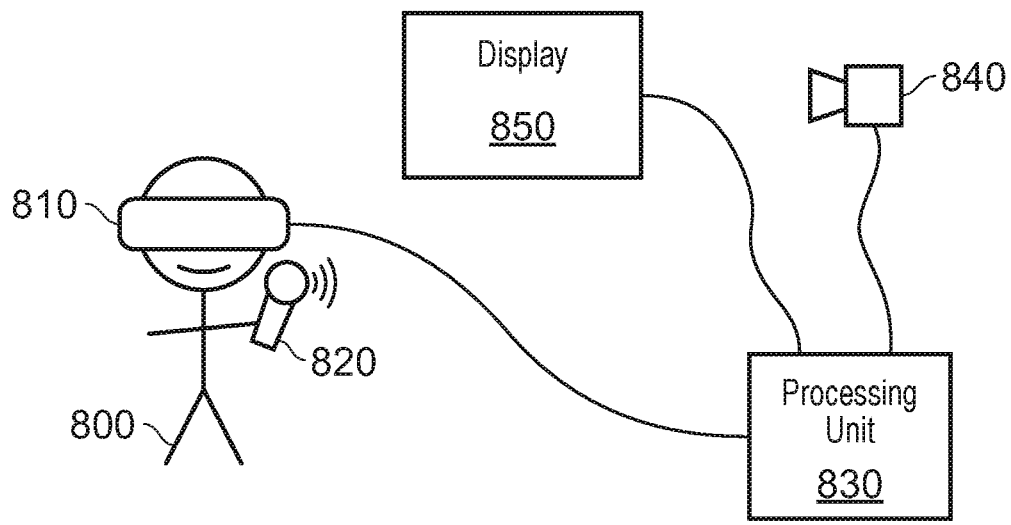
FIG. 8 schematically illustrates a gaze tracking environment.

FIG. 8 schematically illustrates an environment in which an eye-tracking process may be performed. In this example, the user 800 is using an HMD 810 that is associated with the processing unit 830, such as a games console, with the peripheral 820 allowing a user 800 to input commands to control the processing. The HMD 810 may perform eye tracking in line with an arrangement exemplified by FIG. 6a or 6b, for example—that is, the HMD 810 may comprise one or more cameras operable to capture images of either or both of the user's 800 eyes. The processing unit 830 may be operable to generate content for display at the HMD 810; although some (or all) of the content generation may be performed by processing units within the HMD 810.

The arrangement in FIG. 8 also comprises a camera 840, located outside of the HMD 810, and a display 850. In some cases, the camera 840 may be used for performing tracking of the user 800 while using the HMD 810, for example to identify body motion or a head orientation. The camera 840 and display 850 may be provided as well as or instead of the HMD 810; for example these may be used to capture images of a second user and to display images to that user while the first user 800 uses the HMD 810, or the first user 800 may be tracked and view content with these elements instead of the HMD 810. That is to say, the display 850 may be operable to display generated content provided by the processing unit 830 and the camera 840 may be operable to capture images of one or more users' eyes to enable eye-tracking to be performed.

While the connections shown in FIG. 8 are shown by lines, this should of course not be taken to mean that the connections should be wired; any suitable connection method, including wireless connections such as wireless networks or Bluetooth®, may be considered suitable. Similarly, while a dedicated processing unit 830 is shown in FIG. 8 it is also considered that the processing may in some embodiments be performed in a distributed manner—such as using a combination of two or more of the HMD 810, one or more processing units, remote servers (cloud processing), or games consoles.

The processing required to generate tracking information from captured images of the user's 800 eye or eyes may be performed locally by the HMD 810, or the captured images or results of one or more detections may be transmitted to an external device (such as a the processing unit 830) for processing. In the former case, the HMD 810 may output the results of the processing to an external device for use in an image generation process if such processing is not performed exclusively at the HMD 810. In embodiments in which the HMD 810 is not present, captured images from the camera 840 are output to the processing unit 830 for processing.

Figure 9:
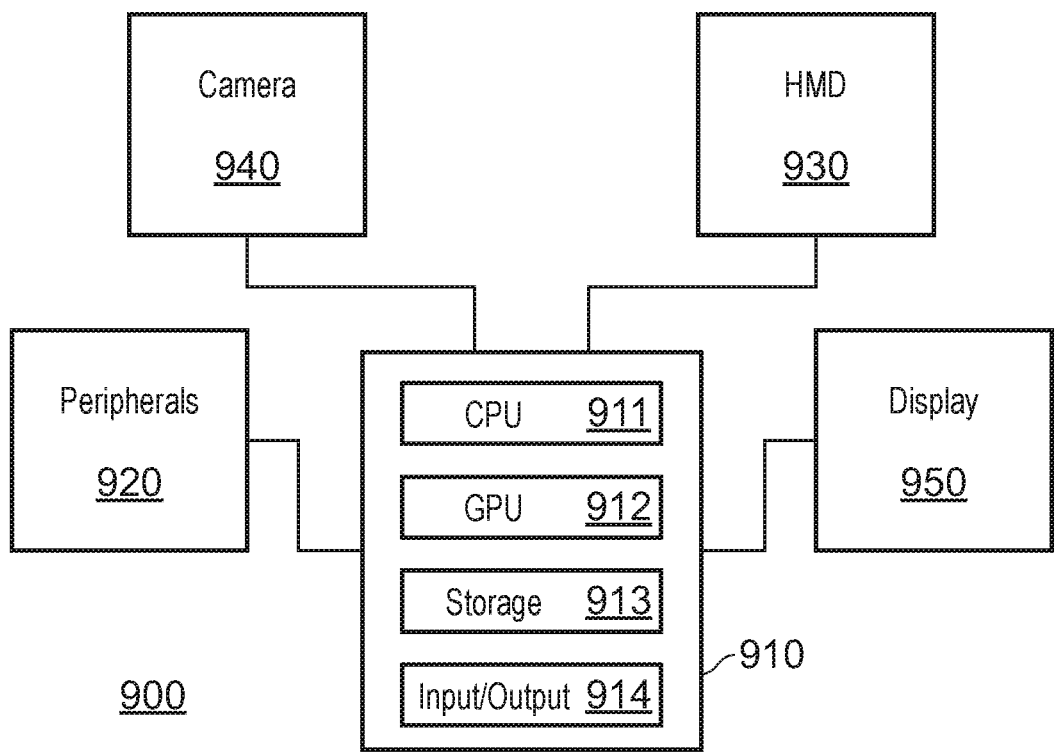
FIG. 9 schematically illustrates a gaze tracking system.

FIG. 9 schematically illustrates a system for performing one or more eye tracking processes, for example in an embodiment such as that discussed above with reference to FIG. 8. The system 900 comprises a processing device 910, one or more peripherals 920, an HMD 930, a camera 940, and a display 950. Of course, not all elements need be present within the system 900 in a number of embodiments—for instance, if the HMD 930 is present then it is considered that the camera 940 may be omitted as it is unlikely to be able to capture images of the user's eyes.

As shown in FIG. 9, the processing device 910 may comprise one or more of a central processing unit (CPU) 911, a graphics processing unit (GPU) 912, storage (such as a hard drive, or any other suitable data storage medium) 913, and an input/output 914. These units may be provided in the form of a personal computer, a games console, or any other suitable processing device.

For example, the CPU 911 may be configured to generate tracking data from one or more input images of the user's eyes from one or more cameras, or from data that is indicative of a user's eye direction. This may be data that is obtained from processing images of the user's eye at a remote device, for example. Of course, should the tracking data be generated elsewhere then such processing would not be necessary at the processing device 910.

The GPU 912 may be configured to generate content for display to the user on which the eye tracking is being performed. In some embodiments, the content itself may be modified in dependence upon the tracking data that is obtained—an example of this is the generation of content in accordance with a foveal rendering technique. Of course, such content generation processes may be performed elsewhere—for example, an HMD 930 may have an on-board GPU that is operable to generate content in dependence upon the eye tracking data.

The storage 913 may be provided so as to store any suitable information. Examples of such information include program data, content generation data, and eye tracking model data. In some cases, such information may be stored remotely such as on a server, and as such a local storage 913 may not be required—the discussion of the storage 913 should therefore be considered to refer to local (and in some cases removable storage media) or remote storage.

The input/output 914 may be configured to perform any suitable communication as appropriate for the processing device 910. Examples of such communication include the transmission of content to the HMD 930 and/or display 950, the reception of eye-tracking data and/or images from the HMD 930 and/or the camera 940, and communication with one or more remote servers (for example, via the internet).

As discussed above, the peripherals 920 may be provided to allow a user to provide inputs to the processing device 910 in order to control processing or otherwise interact with generated content. This may be in the form of button presses or the like, or alternatively via tracked motion to enable gestures to be used as inputs.

The HMD 930 may comprise a number of sub-elements, which have been omitted from FIG. 9 for the sake of clarity. Of course, the HMD 930 should comprise a display unit operable to display images to a user. In addition to this, the HMD 930 may comprise any number of suitable cameras for eye tracking (as discussed above), in addition to one or more processing units that are operable to generate content for display and/or generate eye tracking data from the captured images.

The camera 940 and display 950 may be configured in accordance with the discussion of the corresponding elements above with respect to FIG. 8.

Turning to the image capture process upon which the eye tracking is based, examples of different cameras are discussed. The first of these is a standard camera, which captures a sequence of images of the eye that may be processed to determine tracking information. The second is that of an event camera, which instead generates outputs in accordance with observed changes in brightness.

It is more common to use standard cameras in such tracking arrangements, given that they are widely available and often relatively cheap to produce. 'Standard cameras' here refer to cameras which capture images of the environment at predetermined intervals which can be combined to generate video content. For example, a typical camera of this type may capture thirty images (frames) each second, and these images may be output to a processing unit for feature detection or the like to be performed so as to enable tracking of the eye.

Such a camera comprises a light-sensitive array that is operable to record light information during an exposure time, with the exposure time being controlled by a shutter speed (the speed of which dictates the frequency of image capture). The shutter may be configured as a rolling shutter (line-by-line reading of the captured information) or a global shutter (reading the captured information of the whole frame simultaneously), for example.

However, in some arrangements it may be considered advantageous to instead use an event camera, which may also be referred to as a dynamic vision sensor. Such cameras do not require a shutter as described above, and instead each element of the light-sensitive array (often referred to as a pixel) is configured to output a signal at any time a threshold brightness change is observed. This means that images are not output in the traditional sense—however an image reconstruction algorithm may be applied that is able to generate an image from the signals output by an event camera.

While there is an increased computational complexity for generating an image from such data, the output of the event camera can be used for tracking without any image generation. One example of how this is performed is that of using an IR-sensitive event camera; when imaged using IR light, the pupil of the human eye displays a much higher level of brightness than the surrounding features. By selecting an appropriate threshold brightness, the motion of the pupil would be expected to trigger events (and corresponding outputs) at the sensor.

Independent of the type of camera that is selected, in many cases it may be advantageous to provide illumination to the eye in order to obtain a suitable image. One example of this is the provision of an IR light source that is configured to emit light in the direction of one or both of the user's eyes; an IR camera may then be provided that is able to detect reflections from the user's eye in order to generate an image. IR light may be preferable as it is invisible to the human eye, and as such does not interfere with normal viewing of content by the user, but it is not considered to be essential. In some cases, the illumination may be provided by a light source that is affixed to the imaging device, while in other embodiments it may instead be that the light source is arranged away from the imaging device.

Figure 10:
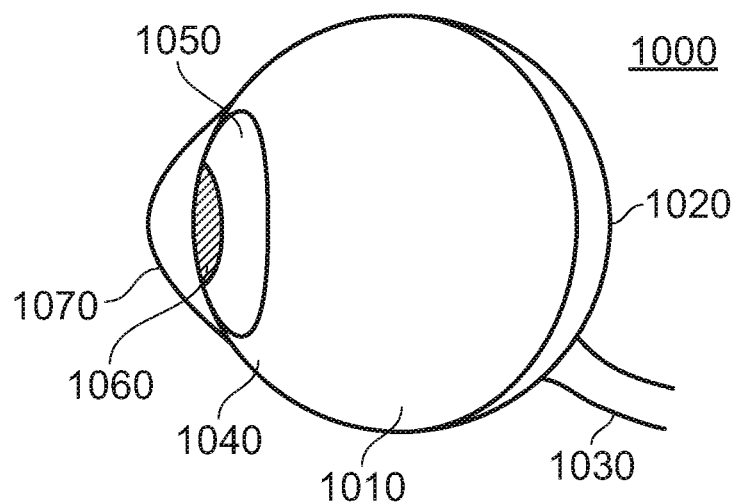
FIG. 10 schematically illustrates a human eye.

As suggested in the discussion above, the human eye does not have a uniform structure; that is, the eye is not a perfect sphere, and different parts of the eye have different characteristics (such as varying reflectance or colour). FIG. 10 shows a simplified side view of the structure of a typical eye 1000; this Figure has omitted features such as the muscles which control eye motion for the sake of clarity.

The eye 1000 is formed of a near-spherical structure filled with an aqueous solution 1010, with a retina 1020 formed on the rear surface of the eye 1000. The optic nerve 1030 is connected at the rear of the eye 1000. Images are formed on the retina 1020 by light entering the eye 1000, and corresponding signals carrying visual information are transmitted from the retina 1020 to the brain via the optic nerve 1030.

Turning to the front surface of the eye 1000, the sclera 1040 (commonly referred to as the white of the eye) surrounds the iris 1050. The iris 1050 controls the size of the pupil 1060, which is an aperture through which light enters the eye 1000. The iris 1050 and pupil 1060 are covered by the cornea 1070, which is a transparent layer which can refract light entering the eye 1000. The eye 1000 also comprises a lens (not shown) that is present behind the iris 1050 that may be controlled to adjust the focus of the light entering the eye 1000.

Figure 11:
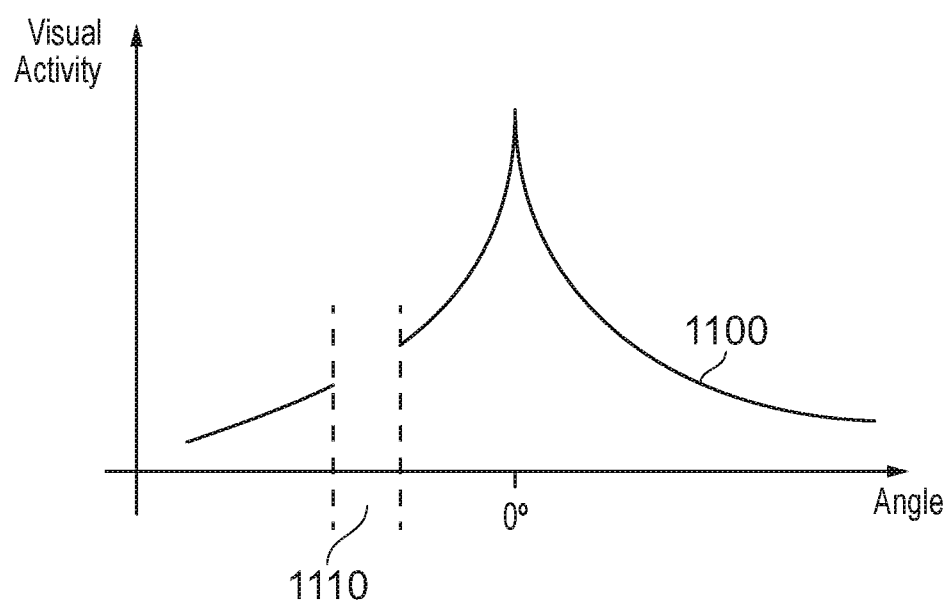
FIG. 11 schematically illustrates a graph of human visual acuity.

The structure of the eye is such that there is an area of high visual acuity (the fovea), with a sharp drop off either side of this. This is illustrated by the curve 1100 of FIG. 11, with the peak in the centre representing the foveal region. The area 1110 is the 'blind spot'; this is an area in which the eye has no visual acuity as it corresponds to the area where the optic nerve meets the retina. The periphery (that is, the viewing angles furthest from the fovea) is not particularly sensitive colour or detail, and instead is used to detect motion.

As has been discussed above, foveal rendering is a rendering technique that takes advantage of the relatively small size (around 2.5 degrees) of the fovea and the sharp fall-off in acuity outside of that.

The eye undergoes a large amount of motion during viewing, and this motion may be categorised into one of a number of categories.

A saccadic eye movement is identified as a fast motion of the eye in which the eye moves in a ballistic manner to change a point of fixation. A saccadic eye movement may be considered as being a ballistic movement in that once the movement of the eye has been initiated to change a point of focus from a current point of focus to a target point of focus (next point of focus), the target point of focus and the direction of movement of the eye to move the point of focus to the target point of focus cannot be altered by the human visual system. Therefore at the time of initiation of the saccadic eye movement, the eye movements to be performed have already been determined and are thus said to be predetermined. During the course of the eye movement to change from the current fixation point to the next fixation point it is not possible to interrupt the eye movement, and upon reaching the target fixation point the eye remains stationary for a period of time (a fixation pause) to focus on the target fixation point before subsequent eye movement can be initiated.

It is sometimes observed that a saccade is followed by a smaller corrective saccade that is performed to bring the eye closer to the target fixation point. Such a corrective saccade typically occurs after a short period of time. As such, saccades can range in size from a small eye movement such as a corrective saccade or a small eye movement made while reading text, for example, to a much larger eye movement made when observing a surrounding environment. Saccades performed when reading text are voluntarily initiated by the human visual system, whereas when surveying a surrounding environment or viewing an image on a display unit saccades are often performed reflexively to focus on a target. Saccades may have a duration of up to approximately two hundred milliseconds, depending on a size of the angle rotated by the eye to change the position of the foveal region of the viewer's vision, but may have a duration as short as twenty milliseconds. Typical rotational velocities for a saccadic eye movement may range from fifty up to seven hundred degrees per second. The rotational velocity of the eye during a saccadic eye movement and the magnitude of the total rotation angle have a relationship in that larger rotational velocities are observed for larger rotation angles.

'Smooth pursuit' refers to a slower movement type than a saccade. Smooth pursuit is generally associated with a conscious tracking of a point of focus by a viewer, and is performed so as to maintain the position of a target within (or at least substantially within) the foveal region of the viewer's vision. This enables a high-quality view of a target of interest to be maintained in spite of motion. If the target moves too fast, then smooth pursuit may instead require a number of saccades in order to keep up; this is because smooth pursuit has a lower maximum speed, in the region of thirty degrees per second.

The vestibular-ocular reflex is a further example of eye motion. The vestibular-ocular reflex is the motion of the eyes that counteracts head motion; that is, the motion of the eyes relative to the head that enables a person to remain focused on a particular point despite moving their head.

Another type of motion is that of the vergence accommodation reflex. This is the motion that causes the eyes to rotate to converge at a point, and the corresponding adjustment of the lens within the eye to cause that point to come into focus.

Further eye motions that may be observed as a part of a gaze tracking process are those of blinks or winks, in which the eyelid covers the eyes of the user.

As discussed previously, a display unit (such as the display element 150, 601) can be provided as part of the HMD and is configured to display images to the user wearing the HMD. Movements of the eye are performed by a user wearing an HMD whilst viewing images displayed by the HMD to enable detailed visual analysis of a portion of an image displayed by the HMD. In particular, the eye can be rotated to reposition the fovea and the pupil to enable detailed visual analysis for the portion of the image for which light is incident upon the fovea.

However, certain eye conditions can cause vision loss either entirely or partially for a portion of the visual field which reduces a user's ability to see for a portion of the eye's visual field. Central vision loss is one of the most common causes of vision loss and macular degeneration is a common type of eye condition that causes central vision loss. Macular degeneration is a type of eye condition associated with damage to a portion of the retina known as the macula that provides the greatest visual acuity. The macula represents a portion of the retina having a diameter of around 5.5 mm for allowing a point of fixation (central vision) for the eye to observed with the highest resolution and highest colour sensitivity available for the eye. The macula is comprised of the fovea, parafovea and perifovea, with the fovea being located at the centre of the macula and being the most sensitive part of the macula corresponding to approximately 5 degrees of the visual field for the eye. Macular diseases can damage parts of the macula such as the fovea thereby leading to a reduction in the level of detail for a portion of the visual field observed by the macula. In some cases, the macula may be damaged to such an extent that a person observes a region of either partially diminished visual acuity or complete blindness (known as a scotoma) in their central vision which is surrounded by otherwise normal vision. Consequently, a fixation point for the eye for which light is incident upon the macula may be perceived as blurred, distorted, indistinct or in some cases a blind spot. Macular degeneration can therefore result in at least partial or complete vision loss for a region of the eye's vision corresponding to the gaze direction of the eye.

Glaucoma is another type of eye condition associated with loss of vision for a portion of the visual field of the eye. In particular, glaucoma is an eye condition associated with damage to the optic nerve which can lead to loss of vision for a peripheral region of the visual field such that the field of vision for the eye is reduced (narrowed). Glaucoma may lead to loss of vision for a peripheral region of the visual field whilst retaining normal high visual acuity for the central region of the visual field. The loss of vision arising from glaucoma can therefore result in a constricted tunnel-like field of vision where the eye is able to rotate to the reposition the pupil and the fovea to observe a point of fixation with high visual acuity but a size of the field of view surrounding the gaze direction is narrowed because vision is lost or significantly reduced for the periphery of the visual field.

Cataracts is another type of eye condition associated with partial or complete loss of vision for a portion of the visual field of the eye due to clouding of the lens of the eye. Different types of cataracts can affect different portions of the lens such as the centre of the lens (nuclear cataracts) or the edges of the lens (cortical cataracts) and may thus affect at least one of the central vison and the peripheral vision for the eye.

Figure 12:
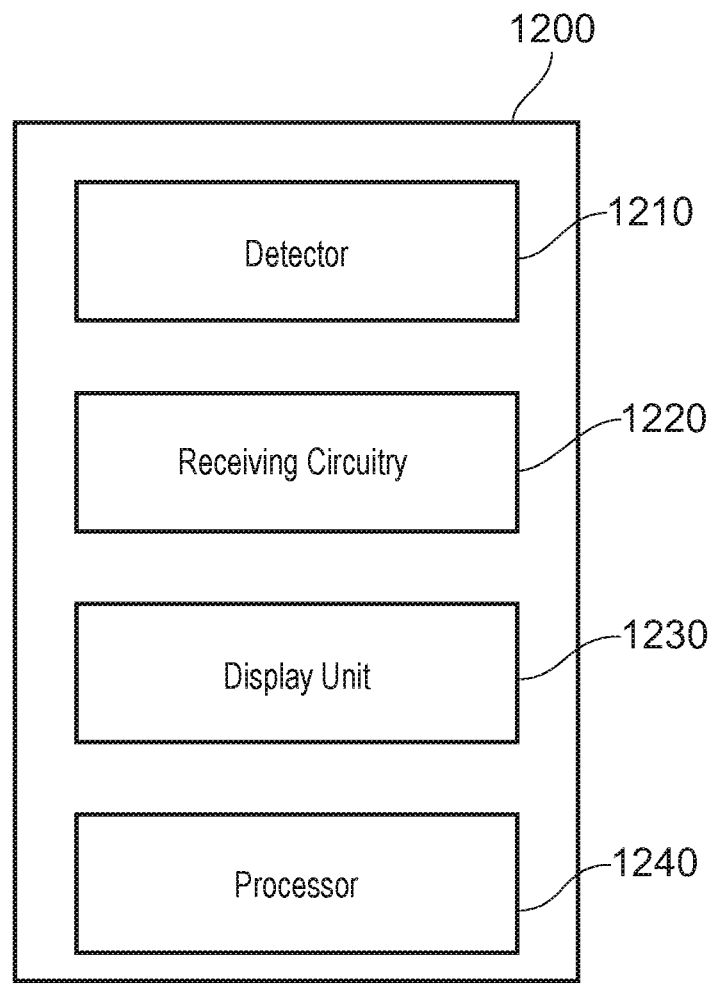
FIG. 12 schematically illustrates an HMD system for generating images for display in dependence upon a type of eye condition.

The operations to be discussed below relate to generating images for display by an HMD in dependence upon a type of eye condition and a gaze direction of an eye of a user wearing the HMD. FIG. 12 schematically illustrates an HMD 1200 for receiving an input from a user wearing the HMD 1200 indicating a type of eye condition associated with at least partial loss of vision for a region of a visual field for an eye of the user and generating images for display in dependence upon the type of eye condition and a detected gaze direction of the eye. In embodiments of the disclosure, the HMD 1200 comprises: at least one detector 1210 to detect a gaze direction of an eye of a user wearing the HMD; receiving circuitry 1220 to receive a user input from the user indicating a type of eye condition for the eye of the user associated with at least partial vision loss for a region of vision; a display unit 1230 to display one or more images to the user; and a processor 1240 to generate the one or more images for display to the user by the display unit in dependence upon the type of eye condition and an output of the at least one detector indicative of the detected gaze direction of the eye.

It will be appreciated however, that optionally the receiving circuitry 1220 and/or the processor 1240 may be located at a separate processing device such as console 830 or 910, or such a device may share their functionality. References herein to the receiving circuitry 1220 and/or the processor 1240 of the HMD 1200 thus encompass that this functionality is either provided by the HMD 1200, or for the HMD 1200 by another device, or shared between the HMD and another device. As such, FIG. 12 provides an example of an HMD system in which the detector 1210, receiving circuitry 1220, display unit 1230 and processor 1240 are provided as part of the HMD 1200.

The HMD 1200 includes at least one detector 1210 for detecting a gaze direction of the eye of the user wearing the HMD 1200. As discussed previously with respect to FIG. 6, the HMD 1200 may comprise any number of detectors 1210 each arranged in-front of an eye of the user in the direction of the display unit 1230 so that a given detector 1210 captures an image including a respective eye. In embodiments of the disclosure, the HMD 1200 includes at least one detector 1210 to detect the gaze direction of one of the user's eyes and at least one other detector 1210 to detect a gaze direction of the other eye of the user. Each detector 1210 provided as part of the HMD 1200 is arranged so that a field of view associated with the detector 1210 includes at least the cornea, pupil and iris of the eye to allow detection of the structures associated with the eye. For example, a position of the pupil and reflections associated with the cornea may be detected by the detector 1210, and an output indicative of these properties for the eye can be provided to the processor 1240 to generate images for display by the HMD 1200 in dependence upon the gaze direction for the eye. Other detectable properties associated with the eye may be used by the detector 1210 for detecting the gaze direction. The detector 1210 is thus configured to detect the gaze direction of the eye and to generate an output indicative of the detected gaze direction of the eye. The detector 1210 can be configured to detect the gaze direction of the eye of the user and generate the output indicative of the detected gaze direction such that the gaze direction of the eye can be tracked.

The at least one detector 1210 comprises a camera comprising at least one of a visible light sensor and an infra-red sensor, and the camera is configured to capture images of the eye of the user. Visible light cameras may be used to capture images of the eye and in some cases the visible light emitted by the display unit 1230 may cause detectable reflections in one or more of the cornea and the pupil. Alternatively, infra-red (IR) cameras may be used with one or more light sources for generating IR light to detect reflections associated with the eye.

The HMD apparatus 1200 includes the receiving circuitry 1220 configured to receive the user input from the user indicating a type of eye condition for an eye of the user associated with at least partial vision loss for a region of vision. The type of eye condition indicated by the user input may be a predetermined type of eye condition such as one of macular degeneration, glaucoma and cataracts. Alternatively, the type of eye condition indicated by the user input may be either a first type of eye condition or a second type of eye condition, where the first type corresponds to vision loss for a central region of vision and the second type corresponds to vision loss for a peripheral region of vision. Hence, in some cases the receiving circuitry 1220 is configured to receive a user input indicating either a first type of eye condition corresponding to vision loss for a central region of vision or second type of eye condition corresponding to vision loss for a peripheral region of vision.

For example, a menu may be displayed to the user from which the user can indicate that they have peripheral vision loss or central vision loss. The HMD 1220 can be configured to display an image comprising a first item corresponding to a first type of eye condition associated with vision loss for a central region of the vision and a second item corresponding to a second type of eye condition associated with vision loss for a peripheral region of the vision. Therefore, rather than requiring the user to specify an eye condition, the user can select whether they suffer from peripheral vison loss or central vision loss. A user input can thus be received by the receiving circuitry 1220 indicative of a selection by the user of the first item or the second item to confirm that the user suffers from either central vision loss or peripheral vision loss.

On the basis of the type of eye condition indicated, an area of the visual field for which the user has vision loss can therefore be identified. For example, when the user confirms that they have macular degeneration the user is identified as having vision loss for a central region of the visual field, whereas when the user confirms that they have glaucoma the user is identified as having vision loss for a peripheral region of the visual field. In some examples, the HMD 1200 may display an image to the user indicating a plurality of types of eye condition and a user input can be received by the receiving circuitry 1220 indicative of a selection by the user of one of the plurality of types of eye condition.

The user input received by the receiving circuitry 1220 may therefore directly indicate either that the user suffers from peripheral vision loss or that the user suffers from central vision loss. Hence more generally, the user input received by the receiving circuitry 1220 is indicative of at least one of the following: the user has partial vision loss for a peripheral region; the user has partial vision loss for a central region; the user has a type of eye condition associated with partial vision loss for a peripheral region; and the user has a type of eye condition associated with partial vision loss for a central region.

For example, the user may press a button on a handheld controller such as the Sony® Move® controller to select a type of eye condition and an output signal from the controller indicative of the button press can be received by the receiving circuitry 1220 which may be provided as part of the HMD 1200 or a separate processing device such as console 830 or 910. Alternatively or in addition, the user may perform a gesture with such a controller which is detectable by at least one of an image capture device or a hardware motion sensor in the controller, and the receiving circuitry 1220 is configured to receive an output signal from at least one of the image capture device and the hardware motion sensor as the user input. For example, the image capture device may be provided as part of the HMD 1200 (e.g. a front facing camera mounted on the HMD) or as part of another information processing device (e.g. a camera mounted in front of the user to capture images of the user). Similarly, a hardware motion sensor provided as part of the HMD 1200 can be configured to detect head movement performed by the user for selecting a type of eye condition and the receiving circuitry 1220 can be configured to receive an output signal from the hardware motion sensor. In some examples, the HMD 1200 may comprise one or more microphones and the user input may be a speech input indicating a type of eye condition for the user.

A user input indicative of a type of eye condition for an eye of the user wearing the HMD 1200 is thus received by the receiving circuitry 1220 indicating that the user is visually impaired. The processor 1240 can therefore generate images for display to the user according to the type of eye condition so as to compensate for a region of vision loss for the eye of the user. The receiving circuitry 1220 is configured to receive the user input indicating the type of eye condition for at least one of the user's eyes and in some examples the user input may specify whether one or both of the eyes have the type of eye condition indicated by the user input.

In embodiments of the disclosure, the receiving circuitry 1220 is configured to receive the user input indicating a type of eye condition for the eye of the user that is one of macular degeneration, glaucoma and cataracts. As discussed previously, macular degeneration is a type of eye condition associated with loss of vision for a central region of vision, glaucoma is a type of eye condition associated with loss of vision for a peripheral region of vision and cataracts is a type of eye condition which may affect different parts of the lens resulting in loss of vision for different portions of the field of vision. In some examples, in response to receiving the user input indicating cataracts a subsequent image may be displayed to the user requesting the user to provide a second user input to further specify a portion of the visual field for which vision loss arises due to the cataracts or to specify a sub-type for the cataracts for use in identifying a portion of the visual field for which the user has loss of vision.

In response to receiving the user input indicating a type of eye condition for the user associated with at least partial vision loss for a region of vision, image processing is performed by the processor 1240 to generate images to be displayed by the HMD 1200 having one or more properties that are dependent upon the type of eye condition. The image processing performed in dependence upon the type of eye condition can be performed either in accordance with one or more predetermined parameters for a type of eye condition or in accordance with one or more offset parameters calculated for a user's eye by displaying one or more calibration images to the user wearing the HMD and detecting the user's gaze direction when viewing the one or more calibration images so that images generated in dependence upon one or more of the offset parameters are calibrated according to the user's vision loss. Techniques for calculating one or more offset parameters for the user to calibrate the HMD for the user are discussed in more detail later.

The HMD apparatus 1200 includes the display unit 1230 configured to display image frames to the user wearing the HMD 1200, where the image frames are displayed consecutively and at least partly generated by the processor 1240. The HMD 1200 may comprise communication circuitry (not shown in FIG. 12) configured to receive video signals transmitted to the HMD 1200 from another information processing device such as a personal computer, games machine or a server by a wired or a wireless connection, as discussed previously. The HMD 1200 can be configured to receive the video signals and the processor 1240 is configured to generate images for display by the display unit 1230 according to the received video signals. In some examples, the HMD 1200 is operable to perform a portion of the processing for generating the images for display by the display unit 1230 and another information processing apparatus such as the personal computer, games machine or server is operable to perform another portion of the processing for generating the images for display by the display unit 1230. In this way, the processing for generating the images for display by the HMD 1200 may in some embodiments be performed in a distributed manner using a combination of processing performed by the processor 1240 of the HMD 1200 and one or more other processing units associated with other devices.

The processor (processing circuitry) 1240 is configured to generate the respective image frames for display by the display unit 1230 and references herein to images generated by the processor 1240 refer to generating either stereoscopic images for which left images and right images are displayed to the respective eyes or generating a single image that is displayed to both eyes. The processor 1240 generates the images for display by the display unit 1230 in dependence upon the gaze direction of the eye indicated by the output of the at least one detector 1210 and the type of eye condition for the user. The processor 1240 can be configured to detect a point of attention for an image displayed by the display unit 1230 in accordance with the detected gaze direction. By detecting the point of attention in accordance with the gaze direction, one or more images to be displayed by the display unit 1230 can be generated accordingly by adjusting a position of one or more objects in the one or more images to be displayed. In some examples, the detector 1210 may detect the point of attention in the image displayed by the display unit 1230 in accordance with the detected gaze direction and the output of the detector may be indicative of the point of attention in the image. As such, the point of attention may be detected by either the detector 1210 or the processor 1240, and images can be generated by the processor 1240 according to a position of the point of attention corresponding to the gaze direction.

For users having non-impaired vision the gaze direction typically represents a portion of the visual field for which the user has the highest visual acuity and the extent of the visual field of the eye is defined as approximately 210 degrees in the horizontal direction and approximately 150 degrees in the vertical direction. Some full immersion HMDs have lenses and display units positioned so that images are displayed to cover the field of view of the human eyes. However, for some users with certain types of eye conditions, there may be partial or complete vision loss for the portion of the visual field corresponding to the gaze direction (central vision loss) or there may be partial or complete vision loss for the peripheral region of vision. Therefore, in the case of central vision loss a portion of a displayed image corresponding to the gaze direction may be only partially visible (or not visible at all) as a result of the user's eye condition. Similarly, in the case of peripheral vision loss, a portion of a displayed image corresponding to the user's peripheral vision may be only partially visible (or not visible at all). Therefore, for users having sight loss for a region of vision, one or more images can be generated accordingly to improve the user's ability to discern features in the one or more images.

In embodiments of the disclosure, for an image to be displayed by the display unit 1230, the processor 1240 is configured to adjust a position of one or more objects in the image in dependence upon the type of eye condition and the detected gaze direction. Movements of the eye are performed by a user wearing an HMD whilst viewing images displayed by the HMD to change the gaze direction and thereby move a point of attention with respect to the display unit 1230. For example, saccadic eye movement or smooth pursuit movement may be performed to rotate the eye to change the gaze direction so that a point of attention for the eye is moved with respect to the display unit 1230 configured to display the images. As the gaze direction and the point of attention changes, the region of vision loss for the eye also moves accordingly. Therefore, one or more images can be generated depending on the direction of the gaze and the type of eye condition, which together provide an indication of the where the region of vision loss for the user is located and thereby provides an indication of a region of the display unit corresponding to the region of vision loss. Hence the one or more images can be generated responsive to the position of the region of vision loss for the user as the user moves their eye so that one or more objects can be positioned depending on their position with respect to the region of vision loss for the user.

For a user having a scotoma (or other less severe central vision loss), for example, when the gaze direction moves to the left the scotoma moves to the left along with the gaze direction so that the portion of the vision corresponding to the gaze direction is continually obscured or diminished. In other words, as the gaze direction moves the spot of diminished vision moves to follow the gaze direction. The processor 1240 is configured to detect the point of attention for the detected gaze direction and to generate an image for display to the user by adjusting a position of at least one object for the image with respect to the point of attention to allow at least one object to be positioned at a portion of the image for which the user does not have vision loss. Therefore, the processor 1240 can be configured to generate one or more images for display by adjusting a position of an object in dependence upon the gaze direction to position the object so that the position of the object differs from the position of the point of attention for the detected gaze direction.

Similarly, for a user having an eye condition resulting in tunnel-like vision, when the gaze direction moves the tunnel-like region for which the user has normal vision moves along with the gaze direction and is typically centred on the gaze direction such that a portion of an image outside the tunnel-like region at any given time may not be observed (or observed with poorer visual acuity compared to a non-impaired viewer) and thus one or more objects in the portion of the image may not be observed. The processor 1240 is therefore configured to detect the point of attention for the detected gaze direction and to generate an image to be displayed to the user by adjusting a position of at least one object in the image with respect to the detected point of attention to allow at least one object to be positioned at a region for which the user does not have vision loss.

In embodiments of the disclosure, the processor 1240 is configured to adjust a position of an object in the image by moving the object in a direction away from a position of a point of attention corresponding to the detected gaze direction in response to the type of eye condition being associated with vision loss for a central region of the vision. The processor 1240 can be configured to generate an image to be displayed to the user by adjusting a position of at least one object for the image with respect to the position of the point of attention to move the object in a direction away from the point of attention and therefore towards a region for which the user does not have vision loss. The processor 1240 can be configured to detect when a distance between the position of the point of attention and a position of an object in an image to be displayed is less than a predetermined distance (and/or when an angle between the gaze direction and a direction from the eye to the position of the object in the image to be displayed is less than a predetermined angle), and in response to detecting that the position of the point of attention is within the predetermined distance (and/or the predetermined angle) of the position of the object, the processor 1240 can generate the image to be displayed by the display unit 1230 by changing the position of the object to move the object away from the point of attention to a position that is separated from position of the point of attention by at least the predetermined distance (and/or the predetermined angle). In this way an object can be repositioned to allow the object to be more easily observed by the user. In response to detecting that the object is within the predetermined distance (and/or predetermined angle) the object is moved in a direction so as to increase the separation distance between the position of the object and the position of the point of attention. In some examples, the object is moved to increase the separation distance by moving the object in a direction that is directly opposite a direction from the position of the object to the position of the point of attention so that a total amount of movement for the object can be minimised whilst ensuring that the object is repositioned outside the predetermined distance (and/or predetermined angle).

Figure 13:
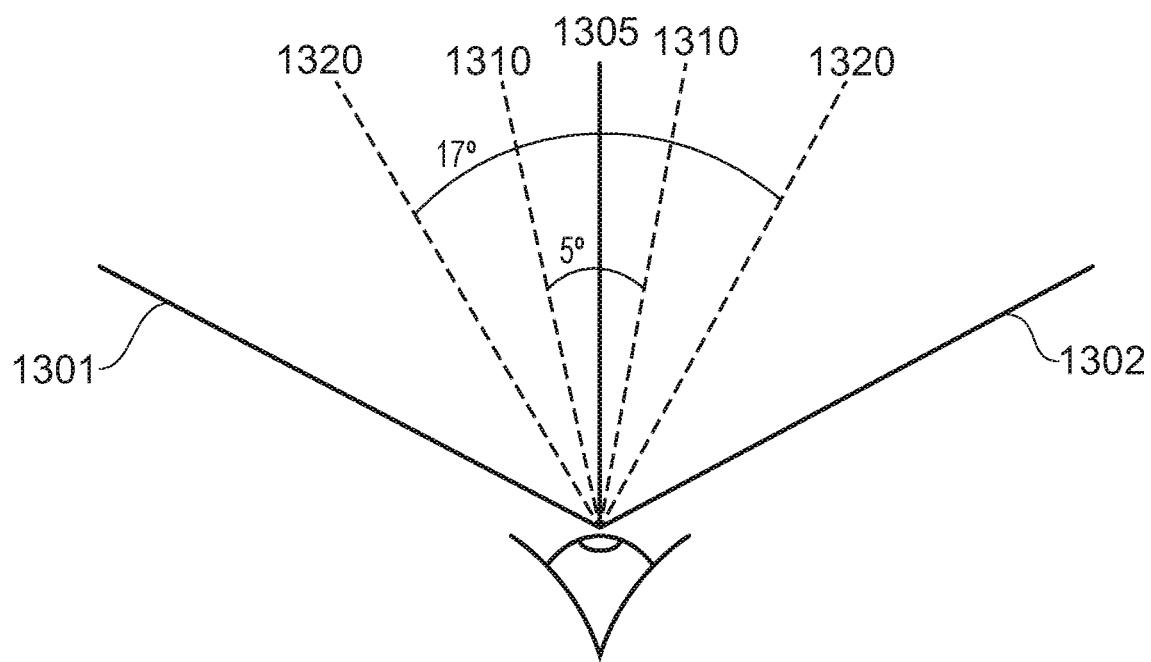
FIG. 13 schematically illustrates a field of view for an eye.

FIG. 13 schematically illustrates an example of a horizontal field of view of an eye in which the solid lines 1301, 1302 represent a limit of the horizontal field of view (or vertical field of view) and the solid line 1305 represents a detected gaze direction of the eye. In this example the detected gaze direction is aligned with the centre of the horizontal field of view and the relative angles are not drawn to scale. The fovea is responsible for approximately 5 degrees of the visual field centred upon the gaze direction while the macula is responsible for approximately 17 degrees of the visual field centre upon the gaze direction. The dotted lines 1310 represent the portion of the field of view for which the fovea is responsible and the dotted lines 1320 represent the portion of the field of view for which the macula is responsible. In some cases a predetermined offset angle in the range 2.5 degrees to 8.5 degrees may be used for adjusting a position of an object, where a predetermined offset angle of 2.5 degrees can be used to reposition an object approximately at the edge of the fovea and a predetermined offset angle of 8.5 degrees can be used to reposition an object approximately at the edge of the macula. For example, for an object having a position that is located within 2.5 degrees of the gaze direction the processor 1240 can be configured to reposition the object to a position such that the object is repositioned at a position within the horizontal field of view that is offset with respect to the gaze direction by at least 2.5 degrees. In the case where the user's fovea suffers from vision loss, this allows an object that would otherwise be positioned within the region of vision loss to be repositioned so as to be observed by a portion of the macula other than the fovea and the ability of the eye to observe the object is thus improved. In some examples, a predetermined offset angle that is greater than 8.5 degrees may be used to reposition the object to a position within the field of view outside the portion of the field of view for which the macula is responsible. By adjusting the position of the target object in this way, the target object can therefore be moved to a position not obscured by the user's vision loss (e.g. scotoma) and the ability of the eye to observe the object is thus improved. As discussed previously, the value of the offset angle may be a predetermined value or may be a value obtained by performing a calibration procedure for the user by displaying calibration images to calculate one or more offset parameters for the user's vision loss.

In some examples, the processor 1240 may be configured to detect when a distance between the position of the point of attention and the position of the object in displayed image is less than a first predetermined distance (and/or first predetermined angle) and if so the processor 1240 can generate an image to be displayed by the display unit 1230 by changing the position of the object to move the object away from the point of attention to a position that is separated from position of the point of attention by at least a second predetermined distance (and/or second predetermined angle), where the first predetermined distance (first predetermined angle) is smaller than the second predetermined distance (second predetermined angle). It will be appreciated that given the geometric arrangement of the user's eye relative to the display unit 1230 of the HMD 1200, at least one of a predetermined angle and a predetermined distance can be used for the predetermined threshold condition where the value for the predetermined angle and the value for the predetermined distance exhibit an interdependence such that using a predetermined angle has the same effect as using a corresponding predetermined distance (a larger value for the predetermined angle corresponds to a larger value for the predetermined distance).

It will be appreciated that for cases where a user suffers vision loss for a larger portion of the visual field a larger value for the predetermined angle and/or the predetermined distance may be beneficial, whereas for cases where a user suffers vision loss for a smaller portion of the visual field a smaller value may be beneficial. Therefore, rather than using a predetermined distance or a predetermined angle as described above, one or more offset parameters may be calculated for a user's eye using a calibration procedure as discussed later so that a user-specific offset distance and/or user-specific offset angle can be used for the condition for determining whether to reposition an object and if so to what extent to reposition the object.

When viewing images displayed by the HMD 1200, the user may perform a saccadic eye movement to quickly move the gaze direction from a current point of attention to a next point of attention where the next point of attention corresponds to an object of interest identified in a displayed image which the user intends to observe in more detail. Such saccadic eye movements may often be performed reflexively to focus on a target object noticed by the user in a peripheral portion of the vision. When performing such a saccade to change from the current fixation point to the target fixation point corresponding to the position of the target object, the ballistic nature of the saccade is such that the position of the target fixation point cannot be changed and therefore the saccade must terminate at the target fixation point. For a user having macular degeneration, performing such a movement of the gaze direction causes the gaze direction to be centred upon the target object and the presence of the scotoma at least partially obscures the target object at the end of the saccade. The processor 1240 can be configured to detect the point of attention and in response to detecting that the position of the point of attention substantially coincides with the position of the target object in the image, the processor 1240 generates one or more images to be displayed by adjusting the position of the target object to a position that is offset from the position for the point of attention by at least the predetermined distance or at least the predetermined angle. Alternatively, one or more offset parameters calculated for the user may similarly be used.

Most people having a scotoma develop a strategy to direct the eyes such that the portion of the image intended for detailed observation actually falls onto a location of the retina different from the fovea and therefore outside of the scotoma (this can therefore result in a misalignment of the gaze direction of the eye and a direction from the eye to an intended observation point for the eye as discussed below). The portion of the retina used for observation in this way is known as the preferred retinal locus (PRL). The PRL is located outside the portion of the retina known as the fovea (outside the normal foveal fixation area) and the PRL represents a portion of the retina that is still capable of normal visual function. The location of the PRL typically varies from one person to another.

When performing saccadic eye movement the user must first perform the saccade to centre the gaze direction upon the target fixation point corresponding to the target object and then perform a subsequent eye movement(s) to offset the gaze direction with respect to the target object so that the target object is positioned outside the scotoma. As such, a number of smaller saccades may need to be performed to bring the target outside the scotoma to the PRL. In some examples, the detector 1210 is configured to detect saccadic eye movement and during the saccadic eye movement the processor 1240 is configured to generate one or more images to be displayed by the display unit 1230 after the termination of the saccade by adjusting the position of the target object according to the predetermined offset angle (and/or predetermined offset distance) or calculated offset angle (and/or calculated offset distance) obtained via calibration to move the target object to a position that is offset from the original position of the target object at the start of the saccade. In this way, when the user performs saccadic eye movement to observe the target object in more detail, the target object is displayed at a position corresponding to the PRL instead of the target fixation point in response to detecting the saccade and this can avoid the need for the user to perform one or more smaller corrective saccades subsequent to the initial saccade to bring the target object to the PRL. Given that a saccade is ballistic in that the direction and the target fixation point cannot be changed once the saccade is initiated, an intended target object for the saccade can be predicted based on a detection of the initial direction of the saccade, the starting fixation point of the saccade and a location of one or more target objects, and one or more images for display after the termination of the saccade can be generated in which the position of the intended target object is adjusted accordingly.

Example techniques for detecting saccades in eye movement data and for calculating parameters for saccade detection are discussed in Behrens, F., MacKeben, M. & Schröder-Preikschat, W., "An improved algorithm for automatic detection of saccades in eye movement data and for calculating saccade parameters", Behaviour Research Methods, 2010, 42(3), 701-708. Other example techniques for detecting saccades are discussed in Wyatt, H "Detecting saccades with jerk", Vision research, Vol. 38, 2147-2153, 1998. The contents of these disclosures are incorporated by reference into this description in their entirety.

For example, a predetermined angular velocity threshold of 50 degrees per second may be selected for comparison with the detection results from the detector 1210, such that when the detection results indicate an angular velocity greater than 50 degrees/second the control circuitry 1220 is configured to detect that the detected eye movement is saccadic eye movement. It will be appreciated that a predetermined angular acceleration threshold (degrees/sec$^2$) and/or a predetermined angular jerk threshold (degrees/sec$^3$) can be employed in a similar manner to that described above for the predetermined angular velocity threshold. By comparing properties of the rotation of the user's eye with one or more thresholds in this way the onset of saccadic eye movement can be detected and the termination of the saccadic eye movement can be detected, and one or more images can be generated for display after the saccade for which a position of a target object is adjusted with respect to an initial position of the target object at the start of the saccade using the predetermined offset angle (and/or predetermined offset distance).

In embodiments of the disclosure, the processor 1240 is configured to move an object in the direction away from the position of the point of attention by adjusting a viewpoint of a virtual camera for the image. The processor 1240 can adjust a position of an object in an image to be displayed by adjusting a viewpoint of a virtual camera for the image. As discussed above, a position of an object may be adjusted to offset the position of the object with respect to a detected gaze direction so that the object is positioned outside a region of vision loss for the eye (e.g. scotoma). Rather than generating one or more images to be displayed by adjusting a position a respective object depending on the position of the object with respect to the gaze direction, a viewpoint for a virtual camera associated with images generated by the processor may be rotated so as to shift the entire image and thereby change the position of the object to a position located outside the region of vision loss for the eye. In this way, the object can be moved to a position outside the region of vision loss for the user and the change in position of the object with respect to the user's gaze direction may be less noticeable for the user because the entire image is moved in the same direction with respect to the user's point of attention. The viewpoint of the virtual camera for the one or more images to be displayed can therefore be controlled depending on whether the position of the point of attention is within the predetermined distance and/or predetermined angle of a positon of an object, and the viewpoint can be rotated horizontally and/or vertically in dependence upon the position of the point of attention to move an object within the predetermined distance and/or predetermined angle of the point of attention in a direction away from the point of attention. Therefore, the processor 1240 can be configured to rotate the viewpoint for the virtual camera according to the predetermined distance and/or the predetermined angle so that the entire image is displaced to move an object to a positon outside the region of vision loss for the user.

In embodiments of the disclosure, the processor 1240 is configured to adjust a viewpoint of a virtual camera for an image to reposition a centre point of a field of view of the virtual camera to a position offset from a centre of the image in response to the predetermined type of eye condition being associated with vision loss for a central region of the vision. Typically a centre point of a field of view of a virtual camera is aligned with a centre of an image because most users have a tendency to direct their eyes towards the centre of the image on the display unit 1230. However, for the case where a user suffers from central vision loss in order to observe the centre point of the image, the user typically has to direct their gaze away from the centre of the image so as to position the centre of the image outside the scotoma. As a consequence of this a user suffering from central vision loss may frequently adopt a gaze direction where the eye is directed away from the centre of the image. The processor 1240 can be configured to adjust a centre point of the field of view of the virtual camera to move the centre point to a position that is displaced from the centre of the image by a predetermined offset distance or a calculated offset distance obtained by performing the calibration procedure for the user. Therefore, the positional relationship between the virtual camera and the displayed images can be adjusted so that when the user's gaze direction is directed towards the centre of the image the centre point of the field of view of the virtual camera is observable at a position that is offset with respect to the gaze direction and thus not obscured by the scotoma.

The processor 1240 can be configured to adjust the viewpoint for the virtual camera for the image to reposition a centre point of a field of view of the virtual camera in dependence upon one or more of the calculated offset parameters for the user obtained from the calibration procedure discussed later. For example, different users may have a different size for their scotoma and a size of the scotoma can be derived using the calibration procedure such that for user's having larger scotomas a larger adjustment for the virtual camera with respect to the image centre can be implemented. In particular, a user having central vision loss may have developed a PRL, where the PRL typically differs from one user to another. As such, a first user may have a PRL such that they prefer the centre point of the field of view of the virtual camera to be displaced to the left of the centre of the image whereas another user may have a PRL such that they prefer the centre point of the field of view of the virtual camera to be displaced to the right of the centre of the image. By performing the calibration procedure and calculating one or more offset parameters for the user both an amount by which the virtual camera is to be displaced relative to the centre of the image and a direction in which the virtual camera is to be displaced can be established for a specific user.

In embodiments of the disclosure, the processor 1240 is configured to adjust a position of an object in the image by moving the object in a direction towards a position of a point of attention corresponding to the detected gaze direction in response to the type of eye condition being associated with vision loss for a peripheral region of the vision. For a user having tunnel-like vision resulting in vision loss for a peripheral region of the vision, the processor 1240 can be configured to generate an image to be displayed to the user by adjusting a position of at least one object in the image with respect to the point of attention to move the object in a direction towards the point of attention and therefore away from a region for which the user has vision loss. In particular, for a user having tunnel-like vision the processor 1240 can be configured to detect when a distance between the position of the point of attention and the position of the object in an image to be displayed is greater than a predetermined distance (and/or when an angle between the gaze direction and the direction from the eye to the position of the object is greater than a predetermined angle), and in response to detecting that the separation distance is greater than the predetermined distance (and/or that the angle between the gaze direction and the direction from the eye to the position of the object is greater than a predetermined angle), the processor 1240 can be configured to generate the image to be displayed by the display unit 1230 by changing the position of the object to move the object in a direction towards the point of attention. In some examples, the processor 1240 is configured to generate the image to be displayed by moving the position of the object towards the point of attention to a final position that is separated from position of the point of attention by at least the predetermined distance (and/or the predetermined angle). In this way, the object can be repositioned to allow the object to be more easily observed by the user having vision loss for a peripheral region of the vision.

The value of the predetermined distance and/or predetermined angle may be selected in advance and may take any value so that for a given point of attention at least a portion of the image is separated from the point of attention by more than the predetermined distance and/or predetermined angle. The value of the predetermined distance may be selected so as to define a circle centred on the point of attention and having a radius equal to the predetermined distance, such that the circle is a predetermined approximation of the size of the user's region of normal vision. An object falling outside the user's region of normal vision can therefore be repositioned in images generated by the processor 1240 to a position that is separated from position of the point of attention by at least the predetermined distance and/or predetermined angle. Therefore, an object that would otherwise be positioned outside the tunnel-like region of normal vision and thus difficult to observe can be moved to a position within the tunnel-like region of vision. In some examples a first predetermined distance may be used for determining whether to adjust a position of an object and a second predetermined distance may be used for defining a final separation distance between the position of the object and the position of the point of attention. It will be appreciated that the severity of the peripheral vision loss, and thus the size of the region of vision loss, may vary from one user to another and therefore rather than using a predetermined distance or a predetermined angle as described above, one or more offset parameters may be calculated for a user's eye using a calibration procedure as discussed later so that a user-specific distance and/or user-specific angle can be used for the condition for determining whether to reposition an object and if so to what extent to reposition the object.

In embodiments of the disclosure, the display unit 1230 is configured to display one or more calibration images in dependence upon the predetermined type of eye condition, each calibration image comprising a target object. As discussed above, rather than using one or more predetermined parameters to generate images for display by the HMD in dependence upon the type of eye condition, a calibration procedure can be used to calculate one or more offset parameters to be used for generating the images for display by the HMD. As part of the calibration procedure a calibration image comprising one or more target objects is displayed to the user wearing the HMD 1200 and the user's gaze direction is monitored and used for comparison with the location(s) of the target object(s). For example, a target object may be displayed in the form of a shape such as a circle or a square or a cross with a fixed position in the calibration image and the user is tasked with locating the target object with their gaze. Detection results from the detector 1210 are used for comparison with the known position(s) of the target object(s) in the calibration image and used to calculate one or more offset parameters (calibration parameters) for use in generating images for display to the user to improve the user's experience.

In embodiments of the disclosure, the display unit 1230 is configured to display one or more first calibration images for a type of eye condition associated with vision loss for a central region of vision and the display unit 1230 is configured to display one or more second calibration images for a type of eye condition associated with vision loss for a peripheral region of vision. The receiving circuitry 1220 is configured to receive the user input indicative of the type of eye condition and in response to the user input the processor 1240 is configured to generate either one or more first calibration images for display by the display unit 1230 or one or more second calibration images for display by the display unit 1230 as part of a calibration procedure for the user. For the case where the user's central vision is diminished, in order to observe the target object in the calibration image the user may deliberately direct their gaze to a portion of the image that is offset with respect to the position of the target object so that light from the target object is incident on a portion of the retina known as the preferred retinal locus (PRL). Consequently, when the user is actually observing a first point in the image the gaze direction may actually be directed towards another point in the image, and as such a vector representing the gaze direction is actually offset with respect to a vector from the eye to the observed first point in the image. In other words, for users with sight loss affecting the central region of vision, detecting the gaze direction of the eye on the basis of images captured of the eye including the pupil, retina and cornea does not provide a true indication of the user's functioning region of view. The display unit 1230 is configured to display one or more first calibration images for a user having the type of eye condition associated with central vision loss, and a gaze direction for the user when observing the target object is detected and used for comparison with the position of the target object to identify an offset for the detected gaze direction.

For the case where the user's peripheral vision is diminished, in order to observe a target object in the calibration image the user may have to perform a number of saccades to locate the target object because the narrower field of view is such that the user is only able to identify objects in the central-most portion of their view. The display unit 1230 is configured to display one or more second calibration images for a user having peripheral vision loss and a number of saccades and/or an amount of time required for the user to locate the target object can be used to identify a size of the portion of the field of view of the eye for which the user's vision is able to function at any given time. As such, for user's suffering from tunnel-like vision, an approximate size of the field of view for the eye can be identified so that images for display to the user can be generated accordingly.

Therefore, the first calibration images differ from the second calibration images in that the first calibration images are used for calculating one or more offset parameters for a user's eye for calculating a modified gaze direction for the eye based on the detected gaze direction for the eye, whereas the second calibration images are used for calculating one or more offset parameters for defining a size of the region of the user's vision for which the user does not have vision loss.

Figure 14:
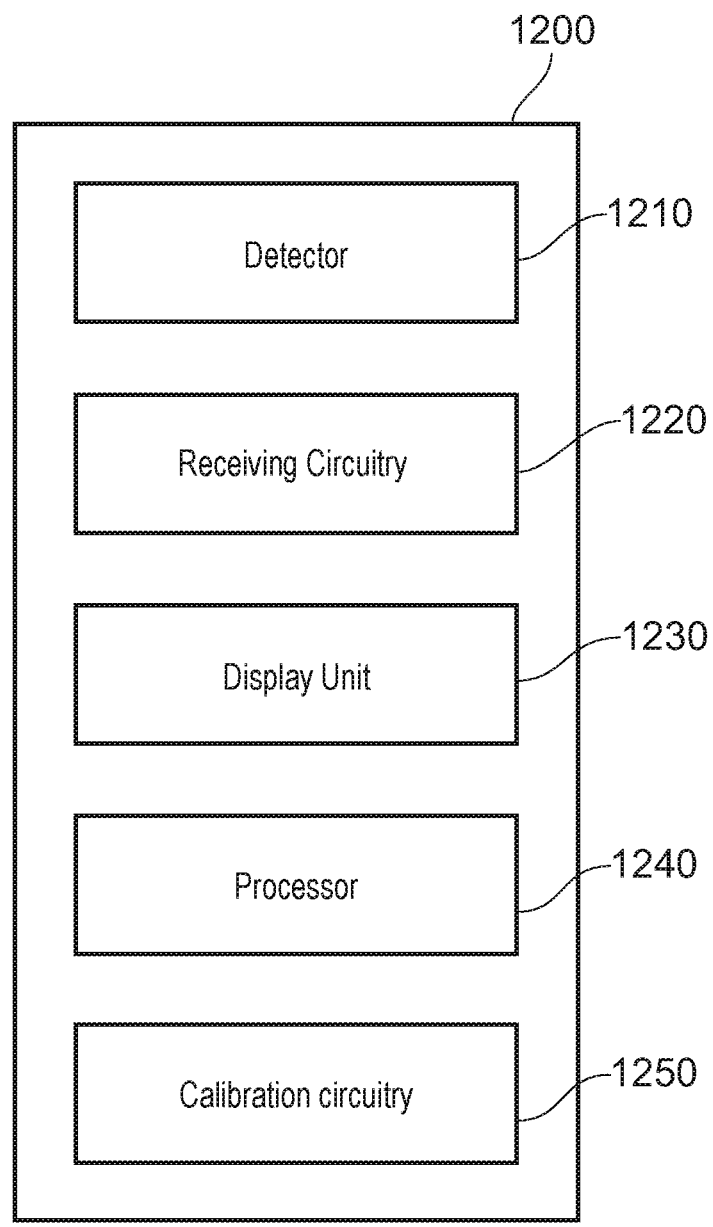
FIG. 14 schematically illustrates an HMD comprising calibration circuitry.

FIG. 14 schematically illustrates an HMD 1200 comprising calibration circuitry. In embodiments of the disclosure, the HMD 1200 further comprises: calibration circuitry 1250 to detect a position of a point of attention in a calibration image in dependence upon the detected gaze direction of the eye and to detect a position of the target object in the calibration image, in which the calibration circuitry 1250 is configured to calculate one or more offset parameters for the eye indicative of an offset for the detected gaze direction in dependence upon a difference between the position of the point of attention and the position of the target object in the calibration image. The receiving circuitry 1220 and/or the processor 1240 and/or the calibration circuitry 1250 may be located at a separate processing device such as console 830 or 910, or such a device may share their functionality. References herein to the receiving circuitry 1220 and/or the processor 1240 and/or the calibration circuitry 1250 thus encompass that this functionality is either provided by the HMD 1200, or for the HMD 1200 by another device, or shared between the HMD and another device.

Figure 15:
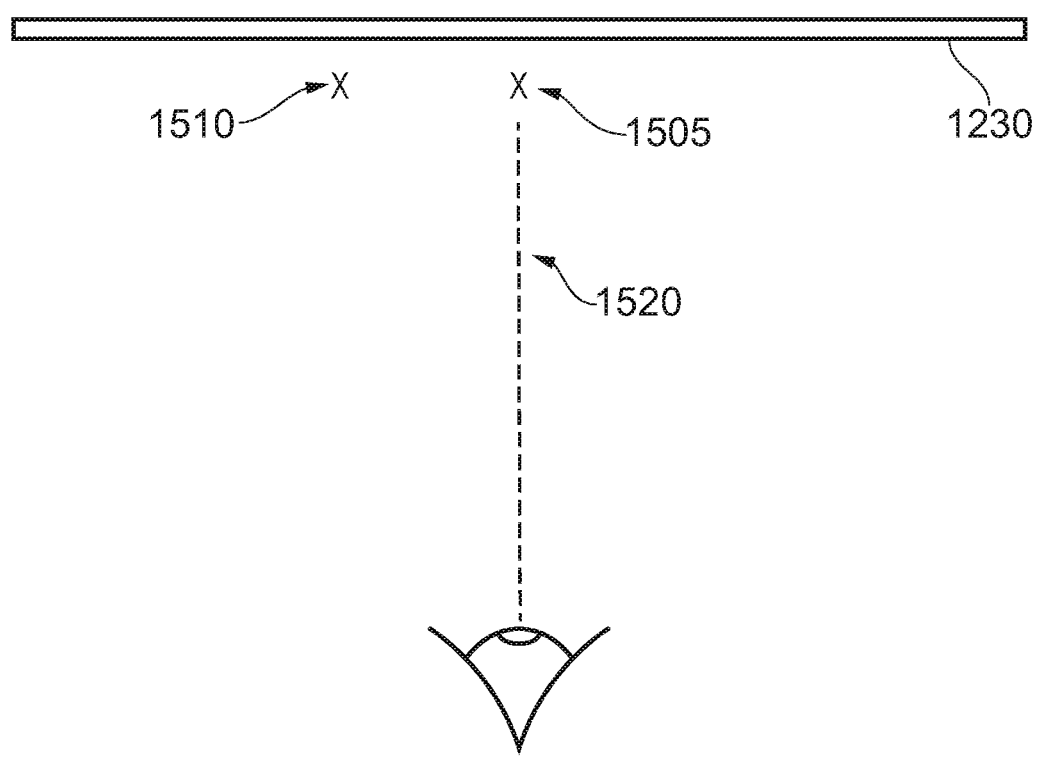
FIG. 15 schematically illustrates a gaze direction of the eye with respect to a calibration image including a target object.

FIG. 15 schematically illustrates a detected gaze direction of the eye when viewing a calibration image including a target object. The display unit 1230 is shown as displaying a calibration image having a target object at a fixed position 1510. In this case the user has central vision loss, such as a scotoma, and therefore deliberately directs their eye in the direction 1520 so that light from the portion of the image corresponding to the position 1510 for the target object is incident on a portion of the retina outside the fovea to allow observation of the target object. Therefore, during the displaying of the calibration image the detector 1210 detects the gaze direction 1520 for the eye corresponding to the point of attention 1505 in the calibration image. However, the target object is in fact located at the position 1510.

The calibration circuitry 1250 is configured to receive the output of the at least one detector 1210 indicative of the detected gaze direction of the eye whilst the calibration image is displayed to the user and to detect the point of attention 1505 in the calibration image. In addition, the calibration circuitry 1250 is configured to detect the position 1510 for the target object in the calibration image. The calibration circuitry 1250 is further configured to compare the position of the point of attention 1505 with the position 1510 for the target object and to calculate one or more offset parameters for the eye. By comparing the position of the point of attention 1505 with the position 1510, a spatial relationship between the detected point of attention 1505 and the user's true observation point 1510 can be established and one or more offset parameters can be calculated indicative of the spatial relationship for the user's eye. Therefore, for a user having central vision loss a true observation point 1510 can be identified for the user based on a detected gaze direction and one or more of the offset parameters calculated for the user. Consequently, rather than the processor 1240 generating images to be displayed by the display unit 1230 according to a position of a point of attention associated with the detected gaze direction, the processor 1240 can be configured to generate one or more images to be displayed according to the user's true observation point by generating the one or more images based on the detected gaze direction for the eye and one or more of the calculated offset parameters for the eye.

In embodiments of the disclosure, the one or more offset parameters comprise at least one of: a parameter defining a spatial separation between the position of the point of attention and the position of the target object in the calibration image; a parameter defining a first offset angle indicative of a deviation between the detected gaze direction and a direction from the eye to the target object in the calibration image with respect to a first axis; and a parameter defining a second offset angle indicative of a deviation between the detected gaze direction and the direction from the eye to the target object in the calibration image with respect to a second axis. Whilst FIG. 15 schematically illustrates a spatial separation between the user's true observation point 1510 (corresponding to the position of the target object) and the detected point of attention 1505 with respect to a single axis (e.g. horizontal axis or vertical axis), it will be appreciated that the user's true observation point may deviate from the detected point of attention in both a vertical direction and a horizontal direction. For example, the user may direct their gaze to right of the true observation point and also downwards of the true observation point so as to direct light form the true observation point onto the preferred retinal locus. In some cases a single offset parameter may be calculated defining a two-dimensional spatial separation between the position of the point of attention and the position of the target object in the calibration image. Alternatively, a first offset parameter indicative of the spatial separation in the a first direction and a second offset to parameter indicative of the spatial separation in the second direction may be calculated for the user to define the spatial relationship between the point of attention and the position of the target object in the calibration image. Alternatively or in addition to calculating an offset parameter defining the spatial separation between the position of the target object and the position of the point of attention, one or more parameters may similarly be calculated for defining one or more offset angles indicative of the deviation between the detected gaze direction and a direction from the eye to the position of the target object.

In embodiments of the disclosure, the processor 1240 is configured to generate the one or more images to be displayed by the HMD 1200 in dependence upon one or more of the offset parameters for the eye. By generating the images in dependence upon one or more of the offset parameters calculated for the user, the images can be adjusted to improve the user's ability to discern features in the one or more images.

In embodiments of the disclosure, the processor 1240 is configured to calculate a modified gaze direction for the eye in dependence upon one or more of the offset parameters for the eye and the output of the at least one detector 1210 indicative of the detected gaze direction of the eye, the modified gaze direction being offset with respect to the detected gaze direction, and in which the processor 1240 is configured to generate the one or more images in dependence upon the modified gaze direction for the eye. The output of the at least one detector 1210 indicative of the detected gaze direction of the eye is provided to the processor 1240, and the processor 1240 is configured to modify the detected gaze direction according to one or more of the offset parameters calculated by the calibration circuitry 1250 so as to obtain the modified gaze direction. At least one of a first offset parameter defining a first offset angle with respect to a first axis and a second offset parameter defining a second offset angle with respect to a second axis may be used to apply an angular offset to the detected gaze direction, such that the modified gaze direction thus represents a direction from the eye to a true observation point for the eye and is deviated with respect to the detected gaze direction.

Figure 16:
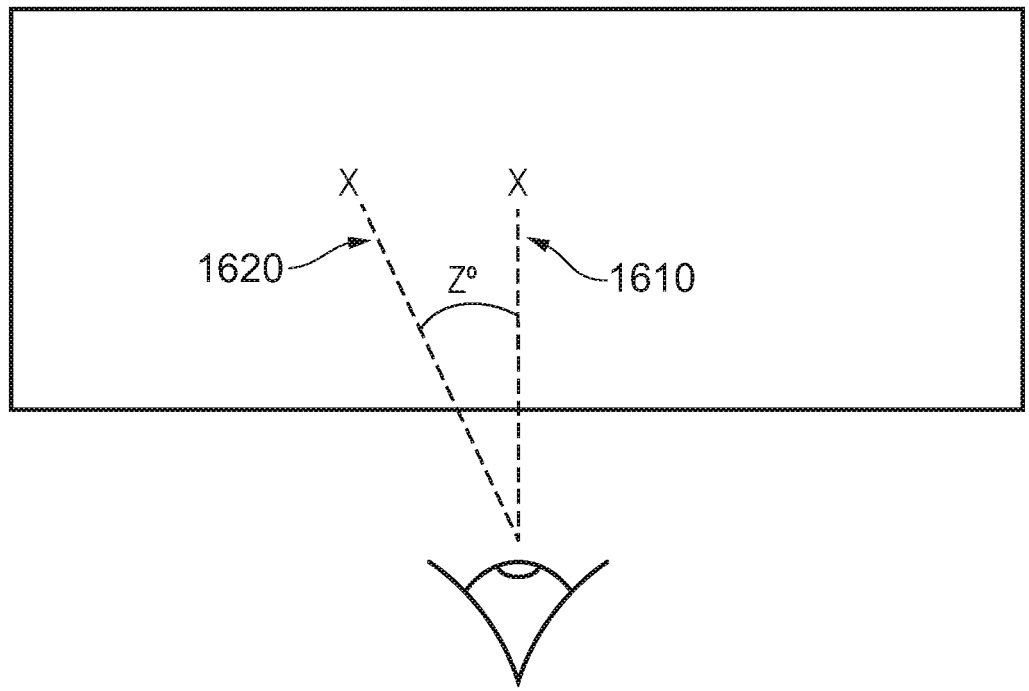
FIG. 16 schematically illustrates a detected gaze direction and a modified gaze direction.

FIG. 16 schematically illustrates a detected gaze direction and a modified gaze direction. In the example shown, the dashed line 1610 represents the detected gaze direction that is detected by the detector 1210, and the dashed line 1620 represents the modified gaze direction that is calculated on the basis of one of more of the offset parameters calculated by the calibration circuitry 1250 and the detected gaze direction 1610. For example, a first offset parameter may define a first offset angle (e.g. Z degrees shown in FIG. 16) with respect to a first axis, and responsive to the output of the detector 1210 the processor 1240 can calculate the modified gaze direction 1620 by rotating the detected gaze direction with respect to the first axis according to the first offset angle such that the modified gaze direction intersects the preferred retinal locus for the user's eye rather than intersecting the fovea. Hence more generally, the detected gaze direction of the eye is arranged to intersect a fovea portion of the retina of the eye and the calculated modified gaze direction for the eye is arranged to intersect a different portion of the retina. Specifically, for a user having a preferred retinal locus the different portion of the retina corresponds to the preferred retinal locus of the retina of the eye. The detector 1210 is configured to detect the gaze direction 1610 for the user's eye in order to track the gaze direction 1610, and the output is provided to the processor 1240 such that as the detected gaze direction 1610 changes the modified gaze direction 1620 is calculated accordingly so as to change with the detected gaze direction 1610 whilst being continually offset with respect to the detected gaze direction 1610 according to the offset defined by one or more of the offset parameters.

Figure 17:
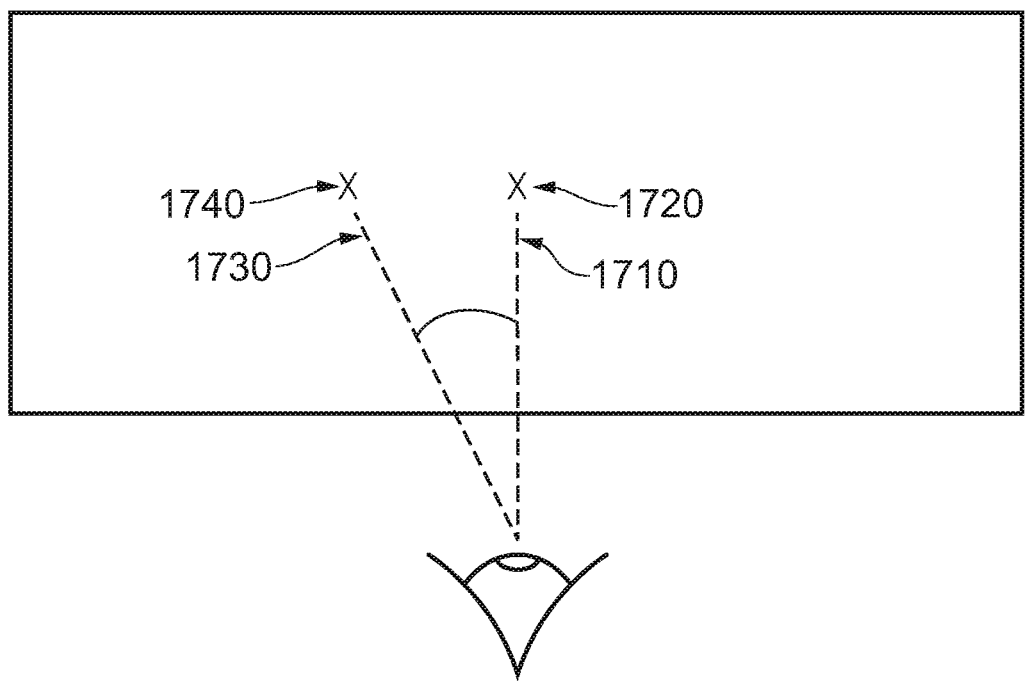
FIG. 17 schematically illustrates calculating a point in an image that is offset with respect to a detected gaze direction.

In embodiments of the disclosure, the processor 1240 is configured to generate the one or more images in dependence upon one or more of the offset parameters for the eye by generating a first portion of an image within a predetermined distance of a first point in the image with a higher image resolution than a second portion of the image not within the predetermined distance of the first point in the image, the first point having a position that is offset from a position of a point of attention in the image corresponding to the detected gaze direction. FIG. 17 schematically illustrates a detected gaze direction 1710 and the corresponding point of attention 1720 as well as a modified gaze direction 1730 and an observation point 1740 for the modified gaze direction. Foveated rendering techniques usually rely on generating a portion of an image centre upon the detected gaze direction with a higher image resolution than other portions of the image. For a user with central vision loss however the detected gaze direction 1710 does not provide a true indication of the user's functioning region of view. Therefore using one or more of the offset parameters calculated by the calibration circuitry 1250, the processor 1240 can be configured to calculate a point 1740 in an image that is offset with respect to the point of attention 1720 using one or more of the offset parameters, where the point 1740 corresponds to the point that is to be observed by the user's preferred retinal locus. The position of the point 1740 may be calculated using at least one of: an offset parameter defining a spatial separation between the position of the point of attention and the position of the target object in the calibration image; and one or more offset parameters defining one or more angular offsets for the detected gaze direction 1710.

The position of the point 1740 may be calculated by detecting the gaze direction 1710 and detecting the point of attention 1720 corresponding to the gaze direction 1710, and applying the offset parameter defining the spatial separation to the point of attention 1720. For example, the offset parameter defining the spatial separation may comprise a first value and a second value indicative on an amount by which the point of attention 1720 is separated from the point 1740 with respect to the X axis and Y axis, respectively, such that the point 1740 can be calculated based on the detected point of attention 1720 and the offset parameter.

By calculating the position of the point 1740 in this way the processor 1240 can generate one or more images for display by generating the portion of the image within the predetermined distance of the point 1740 with a higher image resolution than the portion of the image not within the predetermined distance of the point 1740. Therefore, the portion of the image which is observed by the user's preferred retinal locus can be displayed with a higher image resolution thereby leading to an improvement in the user's ability to discern features in the one or more images whilst also allowing more efficient use of processing resources by allowing the second portion not within the predetermined distance to be generated with a lower image resolution.

As an alternative to the above technique for calculating the position of the point 1740, the position of the point 1740 may be calculated by detecting the gaze direction 1710 and applying one or more offset parameters defining one or more angular offsets to the detected gaze direction 1710 to calculate a modified gaze direction 1730 and thereby calculate the position of the point 1740 corresponding to the modified gaze direction 1730. As such, the processor 1240 can be configured to generate one or more images in dependence upon the modified gaze direction 1730 for the eye by generating a first portion of an image within a predetermined distance of a point 1740 in the image corresponding to the modified gaze direction 1730 with a higher image resolution than a second portion of the image not within the predetermined distance of the point 1740.

In embodiments of the disclosure, the calibration circuitry 1250 is configured to detect a position of a point of attention in a calibration image in dependence upon the detected gaze direction of the eye and to detect a position of the target object in the calibration image, in which the calibration circuitry is configured to calculate one or more offset parameters for the eye indicative of a size of a field of view for the eye in dependence upon at least one of a period of time and a number of saccades for the gaze direction of the eye to locate the target object. For the case where the user's peripheral vision is diminished, in order to observe a target object in the calibration image the user may have to perform a number of saccades to locate the target object because the narrower field of view is such that the user is only able to identify objects in the central-most portion of their view. For example, when the user's gaze direction is directed towards the centre of the calibration image the user's vision loss may be such that the user is unable to observe a target object positioned proximate to the perimeter of the calibration image. Therefore, the display unit 1230 is configured to display one or more second calibration images for a type of eye condition associated with vision loss for a peripheral region of the vision where each second calibration image comprises one or more target objects and a number of saccades performed by the user and/or an amount of time required for the user to visually locate a target object can be detected. The detection results are used to calculate one or more offset parameters defining a size (vertical and horizontal extent) of the visual field for the eye for which the user's vision is able to function at any given time.

The display unit 1230 can be configured to display a plurality of consecutive second calibration images, where each calibration image includes a target object having a fixed position in the calibration image. Upon detecting that the gaze direction for the eye substantially coincides with the position of the target object in the calibration image, a next calibration image is displayed by the display unit 1230. In this way, a starting gaze direction for the user's eye with respect to the next calibration image is known, a position of the target object in the next calibration image is known and the amount of time and/or the number of saccades until the detected gaze direction substantially coincides with the position of the target object in the next calibration image is monitored. By displaying consecutive calibration images each having a target object located at a different position, the user can be tasked with moving their gaze direction to locate the target objects in the respective calibration images. A difference between the positon of the target object in a given calibration image and the position of the target object in a next calibration image and a period of time required for the user to move their gaze direction to substantially coincide with the target object in the next calibration image provides an indication of whether the user's field of view is wider or narrower than the difference in the positions of the two target objects in the two respective calibration images. For example, a time threshold of Y seconds may be used for comparison with the period of time needed by the user to locate a given target object, and if the period of time is less than or equal to the time threshold (indicating that the user was able to see the next target object when the user's gaze was directed towards the position of the previous target object) then the calibration circuitry 1250 calculates an upper limit for the size of the field of view for the eye that is equal to the distance between the position of the target object in the previous calibration image and the position of the target object in the next calibration image. If the amount of time required to locate the target object exceeds the time threshold this is an indication that the target object was initially located outside the user's field of view and that the size of the field of view of the eye is smaller than the distance between the position of the target object in the previous calibration image and the position of the target object in the next calibration image. By displaying consecutive calibration images an extent of the user's field of view in the horizontal direction and the vertical direction can be derived and one or more offset parameters indicative of an angular extent of the field of view can be calculated for the user's eye. In embodiments of the disclosure the one or more offset parameters comprise at least one of a parameter defining an angular range of vision in a first direction, and a parameter defining an angular range of vision in a second direction.

Alternatively or in addition to measuring the period of time for the user to locate the target object, the calibration circuitry 1250 can be configured to detect a total number of saccades required for the user to move their gaze direction from the position of the previous target object to the next target object. In the case where the user is able to locate the next target object by performing a single saccade this indicates that the user was able to see the next target object when the user's gaze was directed towards the position of the previous target object and the calibration circuitry 1250 can be configured to calculate an upper limit for the size of the field of view for the eye that is equal to the distance between the position of the previous target object in the previous calibration image and the position of the next target object in the next calibration image. Therefore by displaying consecutive calibration images and detecting the number of saccades the calibration circuitry 1250 can calculate one or more offset parameters for the eye indicative of the size of the field of view.

In embodiments of the disclosure, the processor 1240 is configured to generate the one or more images to be displayed in dependence upon one or more of the offset parameters for the eye by generating a first portion of an image within a given distance of a point of attention in the image corresponding to the detected gaze direction with a higher image resolution than a second portion of the image not within the given distance of the point of attention. The processor 1240 can be configured to generate one or more images for display in dependence upon one or more of the offset parameters calculated by the calibration circuitry 1250 for a user having peripheral vision loss, where the one or more offset parameters are indicative of the size of the field of view for the eye calculated by displaying second calibration images to the user. The one or more offset parameters therefore define a size of the user's region of normal vision and images can be generated accordingly so that a portion of an image having a size corresponding to the size of the user's functioning field of view is generated with a higher image resolution than a portion of the image outside the user's functioning field of view. In this way the portion of the image for which the user has no vision loss can be generated with a higher image resolution than the portion of the image for which the user has vision loss. In particular, on the basis of the geometric arrangement of the user's eye relative to the HMD 1200, the size of the user's region of normal vision (e.g. angular range of the field of view) can be used to calculate a size for the first portion of the image. Therefore, in response to detecting the point of attention for the gaze direction of the eye, the first portion of the image can be generated so as to be centred upon the point of attention and having a radius of a given distance, where the given distance is calculated based on one or more of the offset parameters. This allows for more efficient use of processing resources given that a portion of the image which is obscured due to vision loss is generated with a lower resolution is therefore less resource intensive to generate.

In embodiments of the disclosure, the calibration circuitry 1250 is configured to calculate a magnitude of the given distance in dependence upon one or more of the offset parameters for the eye. As discussed previously, the one or more offset parameters comprise at least one of a parameter defining an angular range of vision in a first direction, and a parameter defining an angular range of vision in a second direction. The first portion of the image represents a circular portion having a radius that is equal to the given distance. In the case where the offset parameters indicate that the user's region of normal vision is substantially circular such that an angular range with respect to the first direction is substantially the same as an angular range with respect to the second direction, then any one of the parameters can be used to calculate the magnitude of the given distance. In the case where the offset parameters indicate that the user's region of normal vision is not substantially circular, such as when the user's region of normal vision has an elliptical shape that is elongated in the horizontal direction, then the magnitude of the given distance is calculated in dependence upon the offset parameter defining the extent of the field of view in the horizontal direction to allow the first portion of the image to cover the entirety of the user's region of normal vision.

Figure 18:
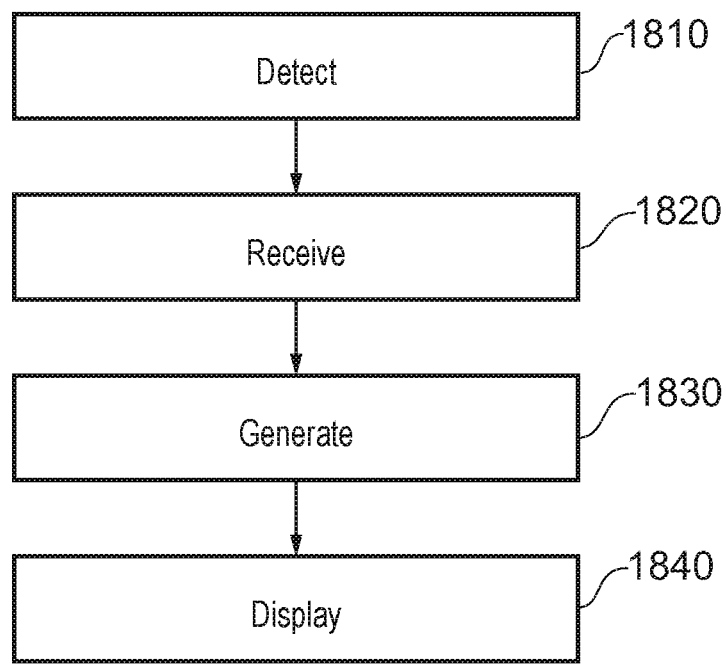
FIG. 18 is a schematic flowchart illustrating a method for generating images for display by an HMD.

Referring now to FIG. 18, in embodiments of the disclosure a data processing method for generating images for display by an HMD, comprises:
- detecting (at a step 1810) a gaze direction of an eye of a user wearing the HMD;
- receiving (at a step 1820) a user input from the user indicating a type of eye condition for the eye of the user associated with at least partial vision loss for a region of vision;
- generating (at a step 1830) one or more images for display to the user in dependence upon the type of eye condition and the detected gaze direction of the eye; and
- displaying (at a step 1840) the one or more images.

It will be appreciated that example embodiments can be implemented by computer software operating on a general purpose computing system such as a games machine. In these examples, computer software, which when executed by a computer, causes the computer to carry out any of the methods discussed above is considered as an embodiment of the present disclosure. Similarly, embodiments of the disclosure are provided by a non-transitory, machine-readable storage medium which stores such computer software.

It will also be apparent that numerous modifications and variations of the present disclosure are possible in light of the above teachings. It is therefore to be understood that within the scope of the appended claims, the disclosure may be practised otherwise than as specifically described herein.

As noted previously herein, optionally the receiving circuitry 1220 and/or processor 1240 may be located at a separate device such as processing unit/console 830 or 910, or such a device may share their functionality with the HMD.

Consequently a head-mountable display (HMD) system may comprise just the head mountable display apparatus, comprising in turn the receiving circuitry 1220 and processor 1240, or it may comprise the head mountable display apparatus and a processing unit/console 830 or 910, implementing or sharing the role of one or both of the receiving circuitry 1220 and processor 1240 in any suitable combination. Similarly, the head mountable display apparatus may comprise the calibration circuitry 1250 or the calibration circuitry 1250 may be provided as part of the processing unit/console 830 or 910.

The foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A head-mountable display (HMD) system comprising:
   at least one detector to detect a gaze direction of an eye of a user wearing an HMD;
   receiving circuitry to receive a user input from the user indicating a selection by the user of a type of eye condition for the eye of the user associated with at least partial vision loss for a region of vision;
   a display unit to display one or more images to the user; and
   a processor that operates to generate the one or more images for display to the user by the display unit in dependence upon the type of eye condition and an output of the at least one detector indicative of the detected gaze direction of the eye, wherein:
   the display unit operates to display one or more calibration images in dependence upon the type of eye condition, each calibration image comprising one or more target objects,
   the display unit operates to display one or more first calibration images in response to the user input indicating a selection by the user of a type of eye condition associated with vision loss for a central region of vision, and
   the display unit operates to display one or more second calibration images in response to the user input indicating a selection by the user of a type eye condition associated with vision loss for a peripheral region of vision.

2. The HMD system according to claim 1, in which the processor operates to adjust a viewpoint of a virtual camera for the image to reposition a centre point of a field of view of the virtual camera to a position offset from a centre of the image in response to the type of eye condition being associated with vision loss for a central region of the vision.

3. The HMD system according to claim 1, in which for an image to be displayed by the display unit, the processor operates to adjust a position of one or more objects in the image in dependence upon the type of eye condition and the detected gaze direction.

4. The HMD system according to claim 3, in which the processor operates to adjust a position of an object in the image by moving the object in a direction away from a position of a point of attention corresponding to the detected gaze direction in response to the type of eye condition being associated with vision loss for a central region of the vision.

5. The HMD system according to claim 4, in which the processor operates to move the object in the direction away from the position of the point of attention by adjusting a viewpoint of a virtual camera for the image.

6. The HMD system according to claim 3, in which the processor operates to adjust a position of an object in the image by moving the object in a direction towards a position of a point of attention corresponding to the detected gaze direction in response to the type of eye condition being associated with vision loss for a peripheral region of the vision.

7. The HMD system according to claim 1, comprising:
   calibration circuitry to detect a position of a point of attention in a calibration image in dependence upon the detected gaze direction of the eye and to detect a position of the target object in the calibration image, in which the calibration circuitry operates to calculate one or more offset parameters for the eye indicative of an offset for the detected gaze direction in dependence upon a difference between the position of the point of attention and the position of the target object in the calibration image.

8. The HMD system according to claim 7, in which the one or more offset parameters comprise at least one of:
   a parameter defining a spatial separation between the position of the point of attention and the position of the target object in the calibration image;
   a parameter defining a first offset angle indicative of a deviation between the detected gaze direction and a direction from the eye to the target object in the calibration image with respect to a first axis; and a parameter defining a second offset angle indicative of a deviation between the detected gaze direction and the direction from the eye to the target object in the calibration image with respect to a second axis.

9. The HMD system according to claim 7, in which the processor operates to generate the one or more images for display to the user by the display unit in dependence upon one or more of the offset parameters for the eye.

10. The HMD system according to claim 7, in which the processor operates to calculate a modified gaze direction for the eye in dependence upon one or more of the offset parameters for the eye and the output of the at least one detector indicative of the detected gaze direction of the eye, the modified gaze direction being offset with respect to the detected gaze direction, and in which the processor operates to generate the one or more images in dependence upon the modified gaze direction for the eye.

11. The HMD system according to claim 10, in which the detected gaze direction of the eye is arranged to intersect a fovea portion of the retina of the eye and the calculated modified gaze direction for the eye is arranged to intersect different portion of the retina.

12. The HMD system according to claim 7, in which the processor operates to generate the one or more images in dependence upon one or more of the offset parameters for the eye by generating a first portion of an image within a predetermined distance of a first point in the image with a higher image resolution than a second portion of the image not within the predetermined distance of the first point in the image, the first point having a position that is offset from a position of a point of attention in the image corresponding to the detected gaze direction in dependence upon one or more of the offset parameters.

13. The HMD system according to claim 1, comprising: calibration circuitry to detect a position of a point of attention in a calibration image in dependence upon the detected gaze direction of the eye and to detect a position of the target object in the calibration image, in which the calibration circuitry operates to calculate one or more offset parameters for the eye indicative of a size of a field of view for the eye in dependence upon at least one of a period of time and a number of saccades for the gaze direction of the eye to locate the target object.

14. The HMD system according to claim 13, in which the one or more offset parameters comprise at least one of a parameter defining an angular range of vision in a first direction, and a parameter defining an angular range of vision in a second direction.

15. The HMD system according to claim 13, in which the processor operates to generate the one or more images in dependence upon one or more of the offset parameters for the eye by generating a first portion of an image within a given distance of a point of attention in the image corresponding to the detected gaze direction with a higher image resolution than a second portion of the image not within the predetermined distance of the point of attention.

16. The HMD system according to claim 15, in which the calibration circuitry operates to calculate a magnitude of the predetermined distance in dependence upon one or more of the offset parameters for the eye.

17. The HMD system according to claim 1, in which the type of eye condition for the eye is one of macular degeneration, glaucoma and cataracts.

18. The HMD system according to claim 1, in which the at least one detector operates to detect the gaze direction of the eye of the user and the HMD system further comprises at least one other detector configured to detect a gaze direction of the other eye of the user.

19. A data processing method for generating images for display by an HMD, comprising:
    detecting a gaze direction of an eye of a user wearing the HMD;
    receiving a user input from the user indicating a selection by the user of a type of eye condition for the eye of the user associated with at least partial vision loss for a region of vision;
    generating one or more images for display to the user in dependence upon the type of eye condition and the detected gaze direction of the eye; and
    displaying the one or more images, wherein:
    the displaying includes displaying one or more calibration images in dependence upon the type of eye condition, each calibration image comprising one or more target objects,
    the displaying includes displaying one or more first calibration images in response to the user input indicating a selection by the user of a type of eye condition associated with vision loss for a central region of vision, and
    the displaying includes displaying one or more second calibration images in response to the user input indicating a selection by the user of a type eye condition associated with vision loss for a peripheral region of vision.

20. A non-transitory, computer readable medium having computer software stored thereon which, when executed by a computer, causes the computer to perform a data processing method for generating images for display by an HMD by carrying out actions, comprising:
    detecting a gaze direction of an eye of a user wearing the HMD;
    receiving a user input from the user indicating a selection by the user of a type of eye condition for the eye of the user associated with at least partial vision loss for a region of vision;
    generating one or more images for display to the user in dependence upon the type of eye condition and the detected gaze direction of the eye; and
    displaying the one or more images, wherein:
    the displaying includes displaying one or more calibration images in dependence upon the type of eye condition, each calibration image comprising one or more target objects,
    the displaying includes displaying one or more first calibration images in response to the user input indicating a selection by the user of a type of eye condition associated with vision loss for a central region of vision, and
    the displaying includes displaying one or more second calibration images in response to the user input indicating a selection by the user of a type eye condition associated with vision loss for a peripheral region of vision.

* * * * *